United States Patent
Grassmann et al.

(10) Patent No.: US 9,562,009 B2
(45) Date of Patent: Feb. 7, 2017

(54) PROCESS TO MANUFACTURE N-[(3S)-1-[4-[(3-FLUOROPHENYL)METHOXY]PHENYL]-5-OXO-PYRROLIDIN-3-YL]ACETAMIDE

(71) Applicant: Hoffmann-La Roche Inc., Little Falls, NJ (US)

(72) Inventors: Olaf Grassmann, Loerrach (DE); Stefan Hildbrand, Gelterkinden (CH); Roland Meier, Ueken (CH); Michelangelo Scalone, Birsfelden (CH); Urs Schwitter, Reinach BL (CH); Beat Wirz, Reinach BL (CH); Ulrich Zutter, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/139,668

(22) Filed: Apr. 27, 2016

(65) Prior Publication Data

US 2016/0237032 A1 Aug. 18, 2016

Related U.S. Application Data

(63) Continuation of application No. PCT/EP2014/072934, filed on Oct. 27, 2014.

(30) Foreign Application Priority Data

Oct. 29, 2013 (EP) .................................... 13190612

(51) Int. Cl.
*C07D 207/273* (2006.01)
*C07C 237/22* (2006.01)

(52) U.S. Cl.
CPC ......... *C07D 207/273* (2013.01); *C07C 237/22* (2013.01); *C07B 2200/13* (2013.01)

(58) Field of Classification Search
CPC .... C07D 207/273; C07C 237/22; C07B 2200/13
USPC ....................................................... 548/550
See application file for complete search history.

(56) References Cited

U.S. PATENT DOCUMENTS 5,272,271 A 12/1993 Seto et al.
7,148,362 B2 * 12/2006 Iding ................... C07D 207/26
548/531

FOREIGN PATENT DOCUMENTS

WO 2004/026825 A1 4/2004
WO 2006/097197 A1 9/2006
WO 2006/097270 A1 9/2006

OTHER PUBLICATIONS

Sánchez V. et al., "Candida antarctica Lipase-Catalyzed Doubly Enantioselective Aminolysis Reactions. Chemoenzymatic Synthesis of 3-Hydorxypyrrolidines and 4-(Silyloxy)-2-oxopyrrolidines withTwo Stereogenic Centers" The Journal of Organic Chemistry 64(5):1464-1470 (Mar. 1, 1999).
Tabei K. et al., "Cyclization of 2-(Gamma-bromoacetoacetamido)pyridine derivatives: Formation of N-aryl-gamma-lactam derivatives." Heterocycles 14(11):1779-1874 (Jan. 1, 1980).

* cited by examiner

*Primary Examiner* — Kristin Vajda

(57) ABSTRACT

The present invention provides processes to manufacture crystalline N-[(3S)-1-[4-[(3-fluorophenyl)methoxy]phenyl]-5-oxo-pyrrolidin-3-yl]acetamide. Also disclosed are compounds useful as intermediates in the methods of the invention.

16 Claims, 13 Drawing Sheets

Raman spectrum – Polymorph B

Fingerprint region

Fingerprint region

US 9,562,009 B2

PROCESS TO MANUFACTURE N-[(3S)-1-[4-[(3-FLUOROPHENYL)METHOXY] PHENYL]-5-OXO-PYRROLIDIN-3-YL]ACETAMIDE

CROSS REFERENCE TO RELATED APPLICATIONS

This application is a continuation of International Application No. PCT/EP2014/072934 having an international filing date of Oct. 27, 2014 and which claims benefit under 35 U.S.C. §119 to European Patent Application No. 13190612.5 filed Oct. 29, 2013. The entire contents of both are incorporated herein by reference.

FIELD OF THE INVENTION

The present invention discloses polymorphic forms of N-[(3S)-1-[4-[(3-fluorophenyl)methoxy]phenyl]-5-oxo-pyrrolidin-3-yl]acetamide. The present invention further provides processes to manufacture crystalline N-[(3S)-1-[4-[(3-fluorophenyl)methoxy]phenyl]-5-oxo-pyrrolidin-3-yl] acetamide, especially in polymorphic form B. Also disclosed are compounds useful as intermediates in the methods of the invention.

BACKGROUND OF THE INVENTION

Alzheimer's disease is a brain disease that slowly destroys memory and thinking skills, up to loss of the ability to carry out the simplest tasks. It is the most common cause of dementia among older people. Mild. Alzheimer's disease manifests itself in memory loss and small changes in other cognitive abilities, e.g., getting lost, trouble handling money and managing daily tasks, having some mood and personality changes, etc. In the stage of Moderate Alzheimer's disease, the control of language, reasoning, sensory processing, and conscious thought are impacted. Memory loss and confusion grow worse, e.g., patients have problems recognizing family and friends and become unable to learn new things, etc. hallucinations, delusions, and paranoia may occur. Severe Alzheimer's disease is the final stage. Patients cannot communicate anymore and are completely dependent on others.

N-[(3S)-1-[4-[(3-fluorophenyl)methoxy]phenyl]-5-oxo-pyrrolidin-3-yl]acetamide has previously been described in WO2001/026825. WO 2006/097197 and WO 2006/097270 relate to methods for preparing enantiomerically pure 4-pyrrolidinophenylbenzyl ether derivatives.

The processes of the prior art have several drawbacks (e.g., long reaction sequence, low overall yield also due to loss of half of the product in the classical resolution step, the need for a chromatographic purification to remove by-products formed in the Mitsunobu reaction) and are therefore less suitable for the preparation of N-[(3 S)-1-[4-[(3-fluorophenyl) methoxy]phenyl]-5-oxo-pyrrolidin-3-yl] acetamide on large scale.

Object of the present invention is to provide an improved and high yielding process which avoids these drawbacks and which is suitable for the large scale manufacture of N-[(3 S)-1-[4-[(3-fluorophenyl)methoxy]phenyl]-5-oxo-pyrrolidin-3-yl]acetamide 1.

BRIEF SUMMARY OF THE INVENTION

The present invention affords polymorphic form A and polymorphic form B of N-[(3S)-1-[4-[(3-fluorophenyl) methoxy]phenyl]-5-oxo-pyrrolidin-3-yl]acetamide 1. The invention further provides a convenient reaction sequence that ultimately affords the title compound in a one step procedure for chlorination and in situ cyclization of (S)-3-acetamido-N-(4-((3-fluorobenzyl)oxy)phenyl)-4-hydroxybutanamide (6).

DETAILED DESCRIPTION OF THE INVENTION

Figure 1:
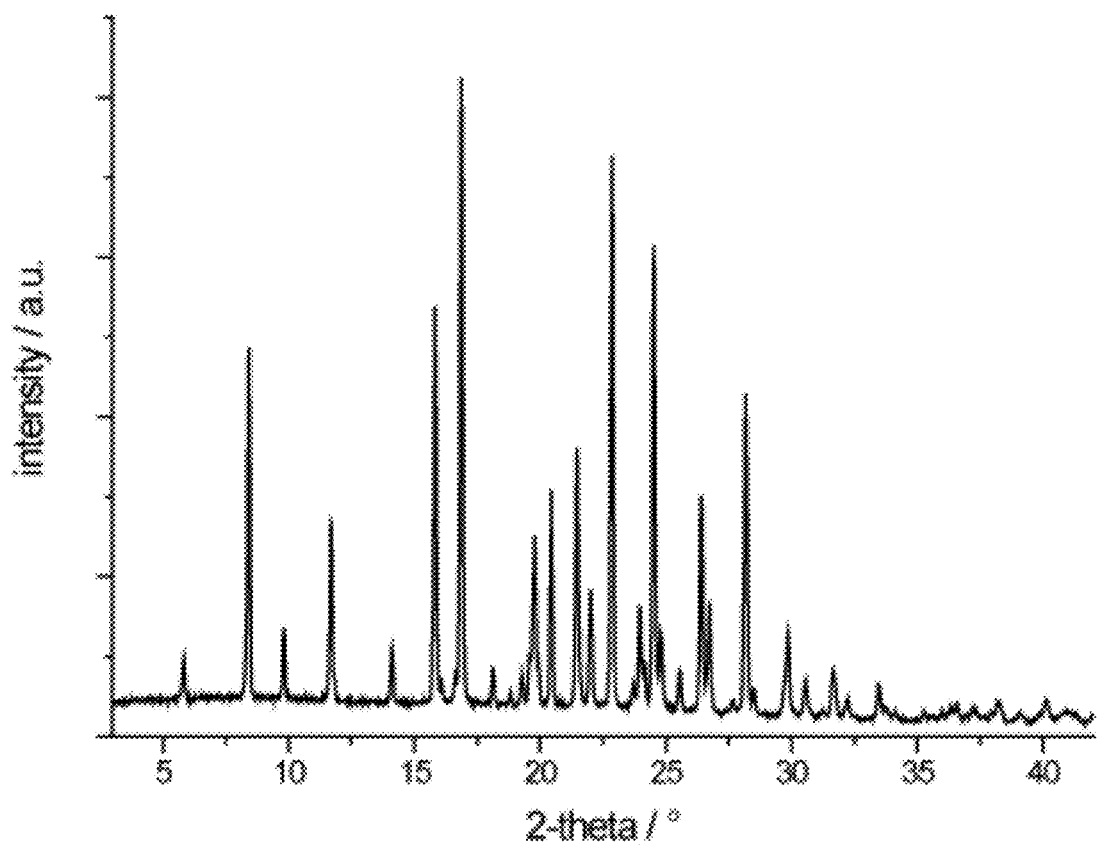
FIG. 1: XRPD pattern of polymorph A of a compound of formula 1.

The following definitions of the general terms used in the present description apply irrespectively of whether the terms in question appear alone or in combination with other groups.

The terms "room temperature" or "ambient temperature" refer to 18-30° C., in particular 20-25° C., more particular to 20° C.

"Solution" as used herein is meant to encompass liquids wherein a reagent or reactant is present in a solvent in dissolved form (as a solute) or is present in particulate, un-dissolved form, or both. Thus, in a "solution", it is contemplated that the solute may not be entirely dissolved therein and solid solute may be present in dispersion or slurry form. Accordingly, a "solution" of a particular reagent or reactant is meant to encompass slurries and dispersions, as well as solutions, of such reagents or reactants. "Solution" and "Slurry" may be used interchangeable herein.

"FTIR" means Fourier Transformed Infrared Spectroscopy.

"XRPD" means X-Ray Powder Diffraction.

"Ac" means acetyl ($CH_3C(=O)$—)

"Amorphous forms" consist of disordered arrangements of molecules that, lacking any long range order and do not possess a crystal lattice, are considered non-crystalline materials.

"Crystal form" is a general term used to refer to polymorphs and pseudopolymorphs of a crystalline solid.

"Solvent" as used herein is meant to encompass liquids that fully dissolve a reagent or reactant exposed to the solvent, as well as liquids which only partially dissolve the reagent or reactant or which act as dispersants for the reagent or reactant. Thus, when a particular reaction is carried out in a "solvent", it is contemplated that some or all of the reagents or reactants present may not be in dissolved form.

The term "approximately" in connection with degrees 2-theta values refers to ±0.2 degrees 2-theta.

The nomenclature used in this Application is based on IUPAC systematic nomenclature, unless indicated otherwise.

The present invention provides quick, efficient and cost effective syntheses of the compound of formula 1, especially polymorphic form B.

In a certain embodiment, the present invention relates to a synthesis of a compound of formula 1 via the following routes

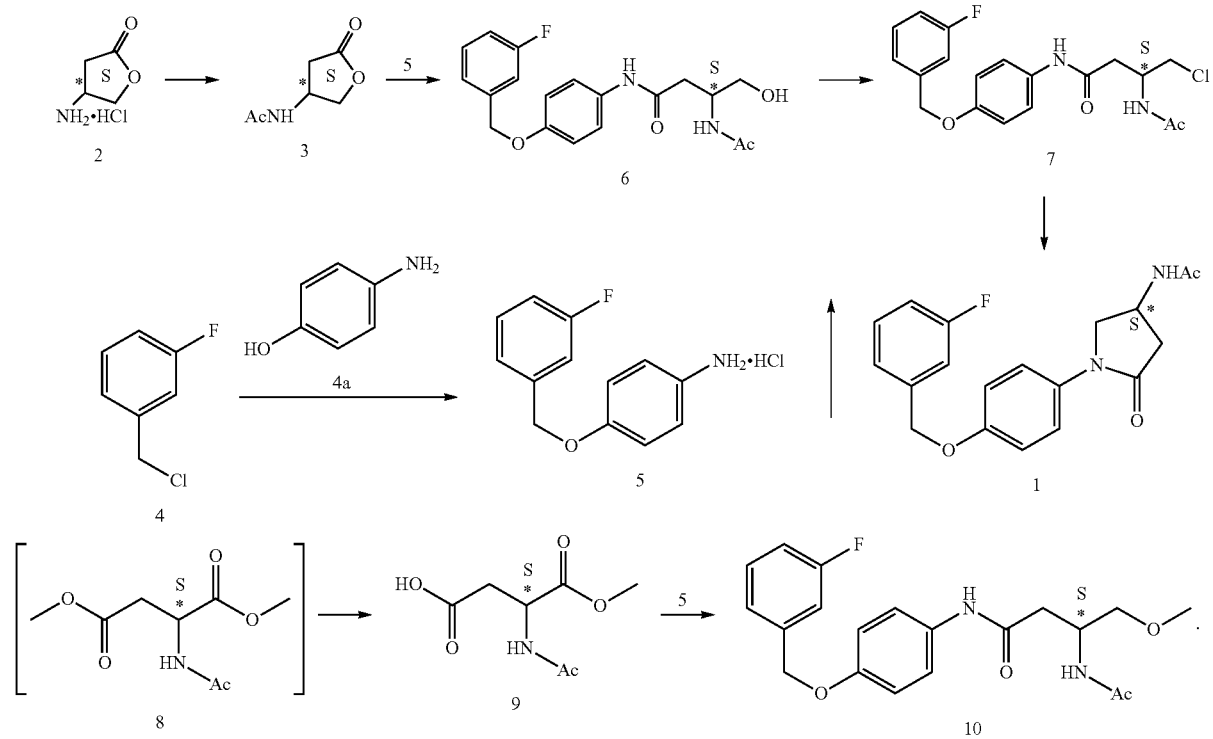

In a certain embodiment, the present invention relates to a synthesis of a compound of formula 1 via the following route A

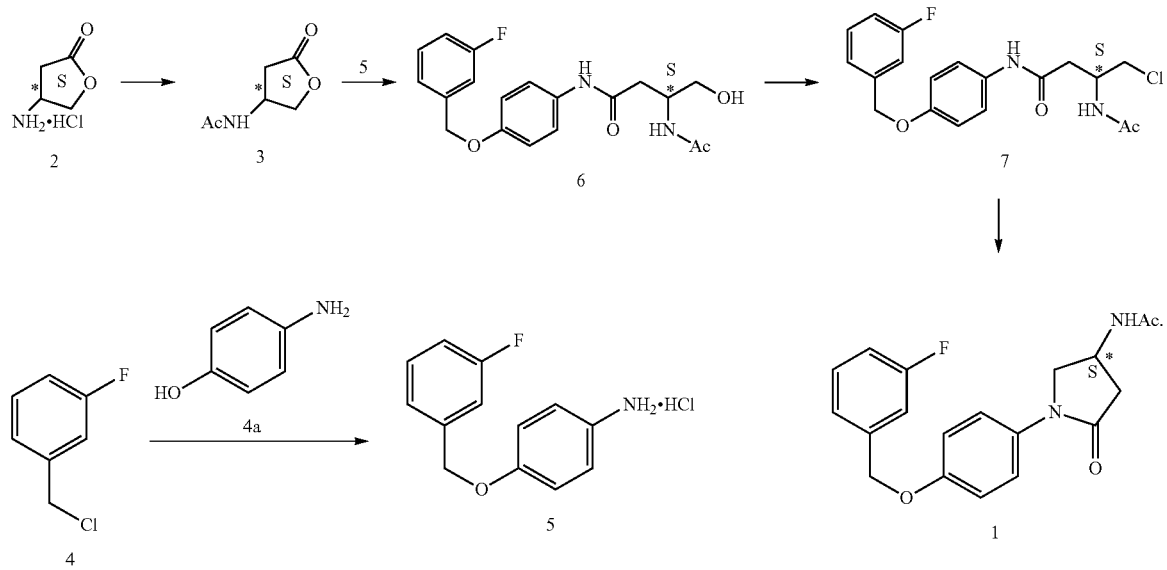

In a certain embodiment, the present invention relates to a synthesis of a compound of formula 1 via the following route B

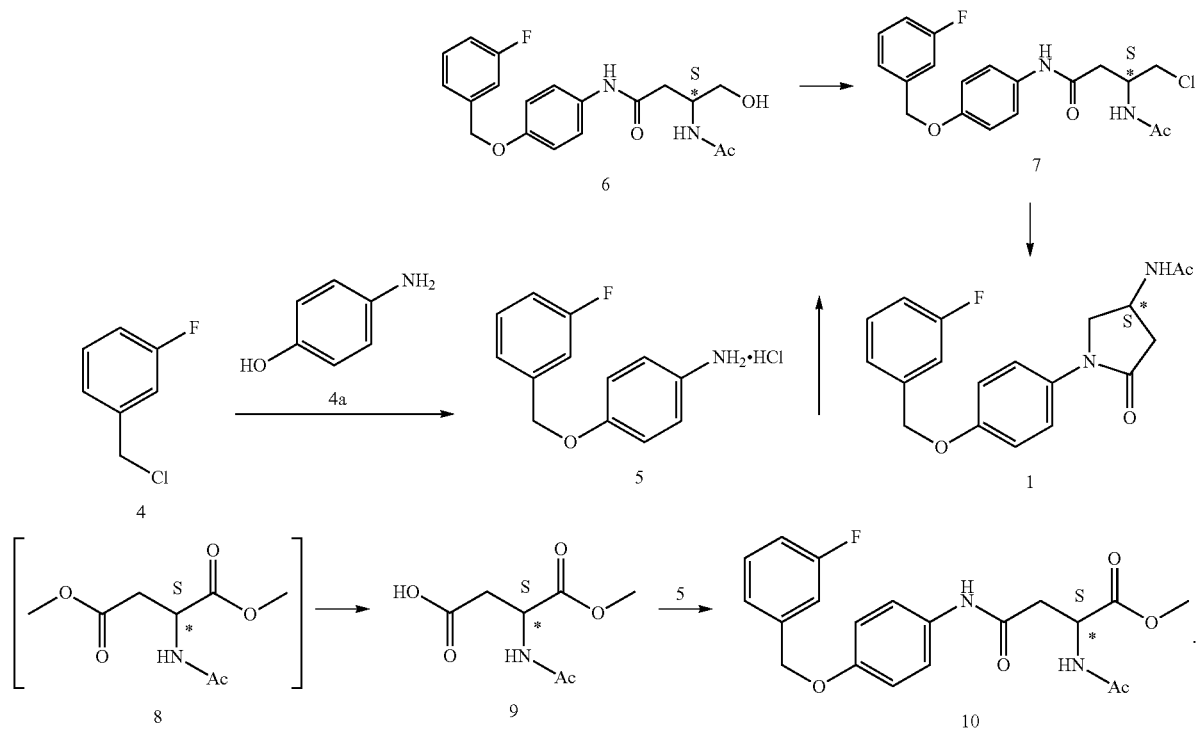

In a certain embodiment, the present invention relates to a crystalline polymorph of a compound of formula 1.

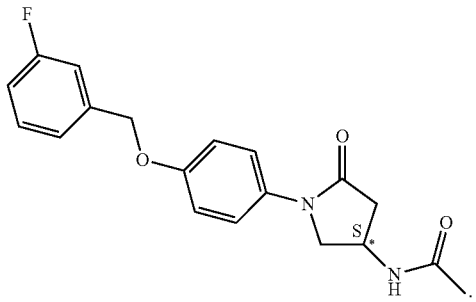

In a certain embodiment, the present invention relates to the crystalline polymorph A of the compound of formula 1, characterized by a X-ray powder diffraction pattern having the characteristic peaks expressed in values of degrees 2-theta at approximately

| degree 2-theta |
|---|
| 5.8 |
| 8.4 |
| 9.8 |
| 11.7 |
| 14.1 |
| 15.8 |
| 16.9 |
| 19.8 |
| 20.4 |
| 21.5 |
| 22.0 |
| 22.9 |
| 24.5 |
| 26.4 |
| 28.2. |

In a certain embodiment, the present invention relates to the crystalline polymorph A of the compound of formula 1, characterized by a X-ray powder diffraction pattern having the characteristic peaks expressed in values of degrees 2-theta at approximately

| degree 2-theta |
|---|
| 8.4 |
| 15.8 |
| 16.9 |
| 22.9 |
| 24.5. |

In a certain embodiment, the present invention relates to the crystalline polymorph A, characterized by the X-ray powder diffraction pattern as shown in FIG. 1.

In a certain embodiment, the present invention relates to the crystalline polymorph B of the compound of formula 1, characterized by a X-ray powder diffraction pattern having the characteristic peaks expressed in values of degrees 2-theta at approximately.

| degree 2-theta |
| --- |
| 11.6 |
| 13.3 |
| 15.9 |
| 16.9 |
| 18.1 |
| 19.7 |
| 20.7 |
| 21.3 |
| 22.5 |
| 23.6 |
| 24.1 |
| 26.7 |
| 27.8 |
| 29.0. |

In a certain embodiment, the present invention relates to the crystalline polymorph B of the compound of formula 1, characterized by a X-ray powder diffraction pattern having the characteristic peaks expressed in values of degrees 2-theta at approximately

| degree 2-theta |
| --- |
| 15.9 |
| 21.3 |
| 23.6 |
| 26.7. |

Figure 4:
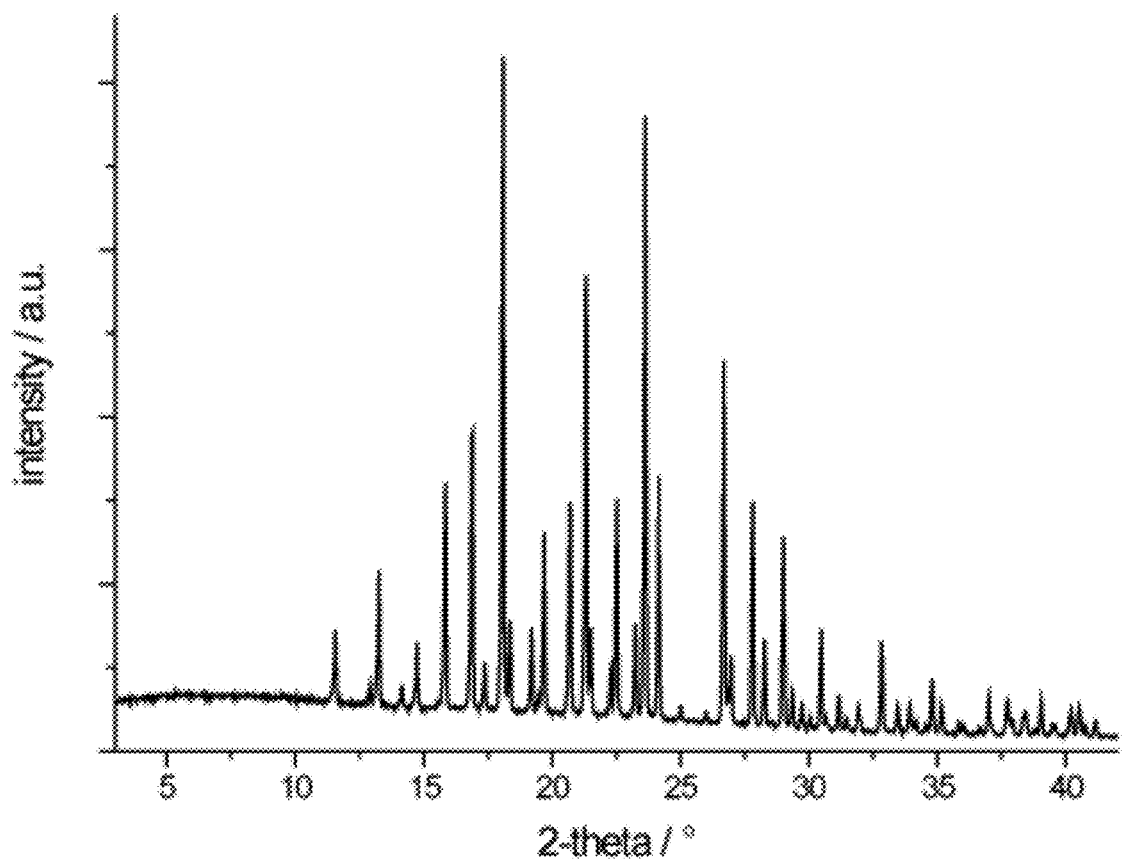
FIG. 4: XRPD pattern of polymorph B of a compound of formula 1.

In a certain embodiment, the present invention relates to crystalline polymorph B, characterized by the X-ray powder diffraction pattern as shown in FIG. 4.

In a certain embodiment, the present invention relates to a process to synthesize a compound of formula 1 from a compound of formula 7

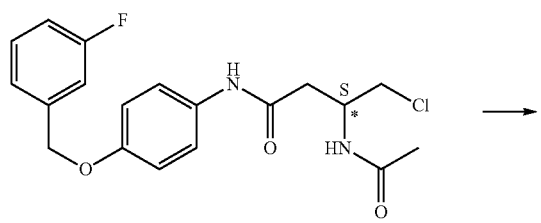

7

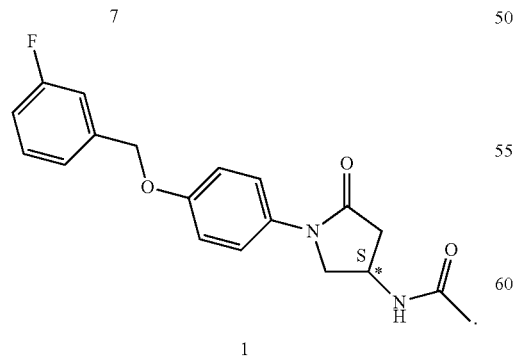

1

In a certain embodiment, the present invention relates to a process to synthesize a compound of formula 1 from a compound of formula 7, whereby the reaction takes place in a suitable solvent like tetrahydrofuran, 2-methyltetrahydrofuran, N-methylpyrrolidone, N-ethylpyrrolidone, dimethylsulfoxide and others (e.g. dimethoxyethane, dimethylformamide), in particular tetrahydrofuran, 2-methyltetrahydrofuran or N-methylpyrrolidone.

In a certain embodiment, the present invention relates to a process to synthesize a compound of formula 1 from a compound of formula 7, using a suitable base like potassium t-butoxide (KOtBu), sodium t-butoxide (NaOtBu), lithium t-butoxide (LiOtBu) and the like, preferably KOtBu.

In a certain embodiment, the present invention relates to a process to synthesize a compound of formula 1 from a compound of formula 7, whereby the reaction takes place between −20° C. to 25° C., in particular between −15° C. to 25° C.

In a certain embodiment, the present invention relates to a process to synthesize a compound of formula 1 as described herein, further comprising reacting a compound of formula 6 to afford a compound of formula 7

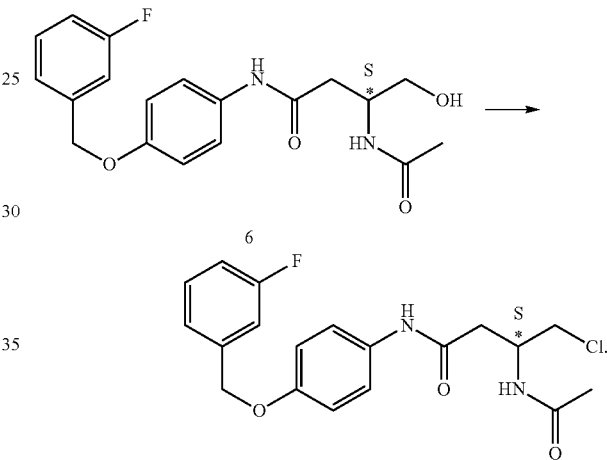

In a certain embodiment, the present invention relates to a process to synthesize a compound of formula 1 as described herein, further comprising reacting a compound of formula 6 via the intermediate 6a to afford a compound of formula 7

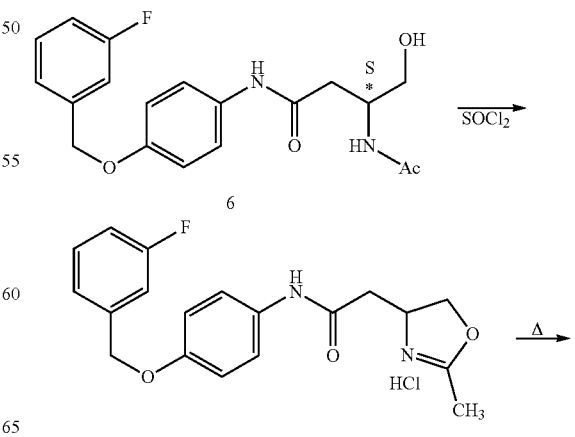

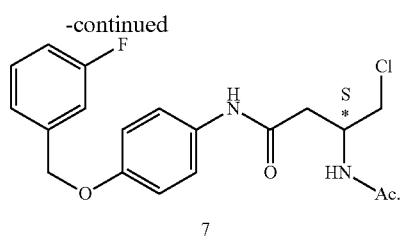

7

In a certain embodiment, the present invention relates to a process to synthesize a compound of formula 1 as described herein, further comprising reacting a compound of formula 6 to a compound of formula 7, whereby the compound 6 is chlorinated with a suitable agent like thionyl chloride, oxalyl chloride or PCl$_5$, in particular thionyl chloride.

In a certain embodiment, the present invention relates to a process to synthesize a compound of formula 1 as described herein, further comprising reacting a compound of formula 6 to a compound of formula 7, whereby the chlorination takes place in a suitable solvent like toluene, ethylacetate, isopropylacetate, n-propylacetate, isobutylacetate or acetonitrile, in particular ethyl acetate (EtOAc) or toluene.

In a certain embodiment, the present invention relates to a process to synthesize a compound of formula 1 as described herein, further comprising reacting a compound of formula 6 to a compound of formula 7, whereby the chlorination takes first place at lower temperatures like 15° C. to 55° C., forming the intermediate 6a, and subsequently at higher temperatures like 70° C. to 80° C. (for EtOAc) or 85° C. to 110° C. (for toluene).

In a certain embodiment, the present invention relates to a process to synthesize a compound of formula 1 as described herein, further comprising reacting a compound of formula 3 with a compound of formula 5 to afford a compound of formula 6

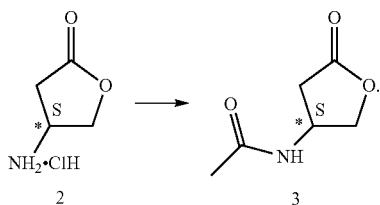

In a certain embodiment, the present invention relates to a process to synthesize a compound of formula 1 as described herein, further comprising reacting a compound of formula 2 to afford a compound of formula 3 in the presence of acetic anhydride.

In a certain embodiment, the present invention relates to a process to synthesize a compound of formula 1 as described herein, further comprising reacting a compound of formula 2 to a compound of formula 3, in the presence of a suitable base like potassium carbonate or sodium carbonate, in particular potassium carbonate.

In a certain embodiment, the present invention relates to a process to synthesize a compound of formula 1 as described herein, further comprising reacting a compound of formula 2 to a compound of formula 3 in a suitable solvent like dichloromethane or acetone, in particular acetone.

In a certain embodiment, the present invention relates to a process to synthesize a compound of formula 1 as described herein, further comprising reacting a compound of formula 10 to afford a compound of formula 6

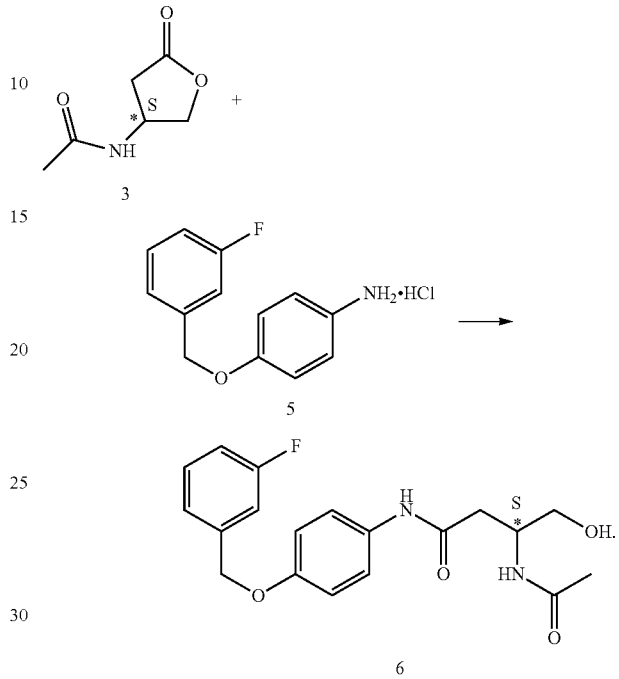

In a certain embodiment, the present invention relates to a process to synthesize a compound of formula 1 as described herein, further comprising reacting a compound of formula 3 with a compound of formula 5 to a compound of formula 6, whereby the reaction is catalysed by a suitable base like sodium ethylhexanoate.

In a certain embodiment, the present invention relates to a process to synthesize a compound of formula 1 as described herein, further comprising reacting a compound of formula 3 with a compound of formula 5 to a compound of formula 6, whereby the reaction takes place in a suitable solvent like toluene, dimethoxyethane, tetrahydrofuran or acetonitrile, in particular toluene.

In a certain embodiment, the present invention relates to a process to synthesize a compound of formula 1 as described herein, further comprising reacting a compound of formula 2 to afford a compound of formula 3

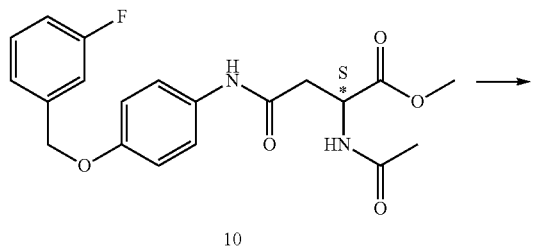

-continued

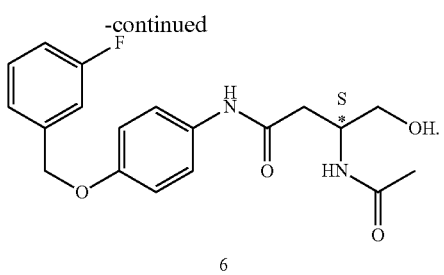

6

In a certain embodiment, the present invention relates to a process to synthesize a compound of formula 1 as described herein, further comprising reacting a compound of formula 10 to afford a compound of formula 6, in the presence of a suitable reducing agent like lithium borohydride (LiBH$_4$).

In a certain embodiment, the present invention relates to a process to synthesize a compound of formula 1 as described herein, further comprising reacting a compound of formula 10 to afford a compound of formula 6, in a suitable solvent like tetrahydrofuran.

In a certain embodiment, the present invention relates to a process to synthesize a compound of formula 1 as described herein, further comprising reacting a compound of formula 10 to afford a compound of formula 6, at a temperature between −10° C. and ambient temperature, in particular at 0° C.

In a certain embodiment, the present invention relates to a process to synthesize a compound of formula 1 as described herein, further comprising reacting a compound of formula 9 with a compound of formula 5 to afford a compound of formula 10

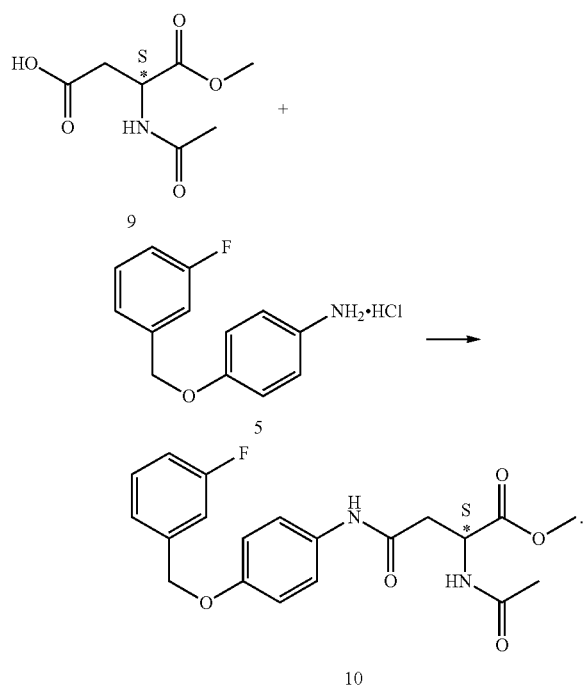

In a certain embodiment, the present invention relates to a process to synthesize a compound of formula 1 as described herein, further comprising reacting a compound of formula 9 with a compound of formula 5 to afford a compound of formula 10, in the presence of a suitable coupling agent like isobutyl chloroformate.

In a certain embodiment, the present invention relates to a process to synthesize a compound of formula 1 as described herein, further comprising reacting a compound of formula 9 with a compound of formula 5 to afford a compound of formula 10, in the presence of a suitable base like 4-methylmorpholine.

In a certain embodiment, the present invention relates to a process to synthesize a compound of formula 1 as described herein, further comprising reacting a compound of formula 8 to afford a compound of formula 9

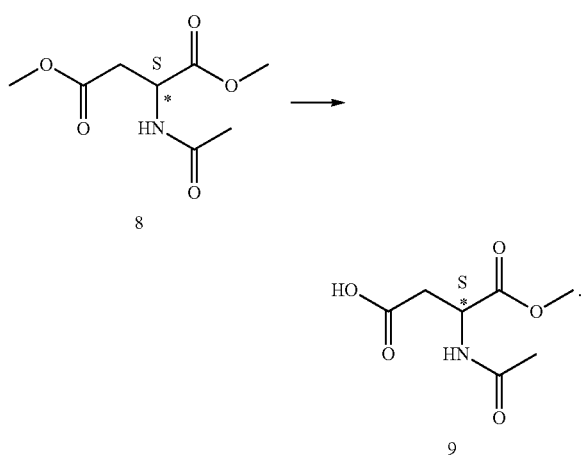

In a certain embodiment, present invention relates to a process to synthesize a compound of formula 1 as described herein, further comprising regioselectively hydrolyzing by an enzymatic reaction a compound of formula 8 to afford a compound of formula 9 in an aqueous buffer at a pH range of 5.0 to 7.5, in particular 5.5 to 6.5.

In a certain embodiment, the present invention relates to a process to synthesize a compound of formula 1 as described herein, further comprising regioselectively hydrolyzing by an enzymatic reaction a compound of formula 8 to afford a compound of formula 9 using enzymes like protease from *Bacillus lentus* or lipase from *Candida antarctica* form B, in particular lipase from *Candida antarctica* form B.

In a certain embodiment, the present invention relates to a process to synthesize a compound of formula 1 as described herein, further comprising regioselectively hydrolyzing by an enzymatic reaction a compound of formula 8 to afford a compound of formula 9 whereby a high substrate concentration is used used like 5-20% w/v, in particular 8-12%, more particular 10%.

In a certain embodiment, the present invention relates to a process to synthesize a compound of formula 1 as described herein, further comprising reacting a compound of formula 4 with a compound of formula 4a to afford a compound of formula 5

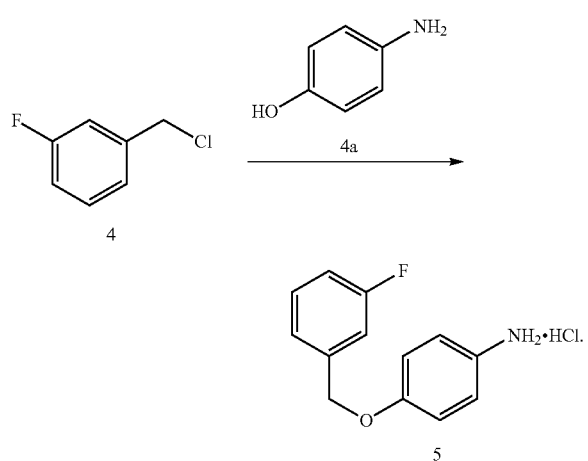

In a certain embodiment, the present invention relates to an intermediate compound 6

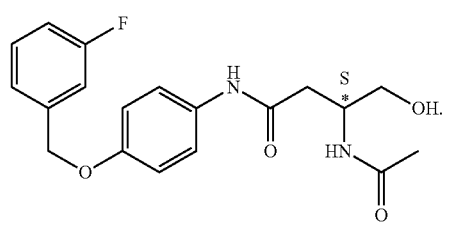

In a certain embodiment, the present invention relates to a process to synthesize a compound of formula 1 as described herein, further comprising reacting a compound of formula 6 to a compound of formula 1 via a compound of formula 7 in a one-pot reaction

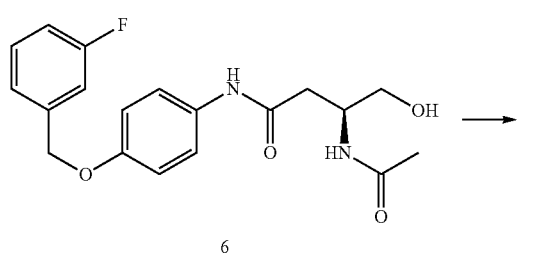

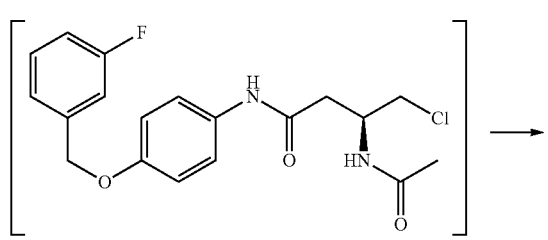

In a certain embodiment, the present invention relates to a process to synthesize a compound of formula 1 as described herein, further comprising reacting a compound of formula 6 to a compound of formula 1 in a one-pot process, whereby the chlorination takes first place in toluene, followed by a solvent exchange to N-methyl-2-pyrrolidone (NMP) wherein the cyclisation takes place.

In a certain embodiment, the present invention relates to an intermediate compound 10

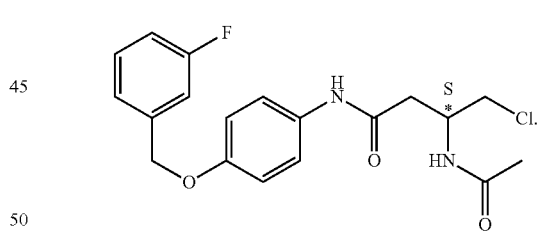

In a certain embodiment, the present invention relates to an intermediate compound 7

In a certain embodiment, the present invention relates to a compound of formula 1, whenever prepared by a process as described herein.

In a certain embodiment, the present invention relates to compound of formula 1 as described herein for use as a medicament.

In a certain embodiment, the present invention relates to compound of formula 1 as described herein for use in the therapeutic and/or preventive treatment of Alzheimer's Disease.

In detail, the present invention provides a process to synthesize a crystalline polymorph of a compound of formula 1

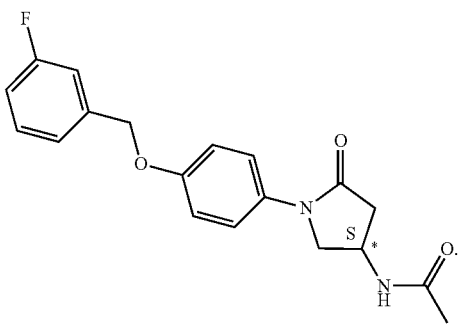

Figure 2:
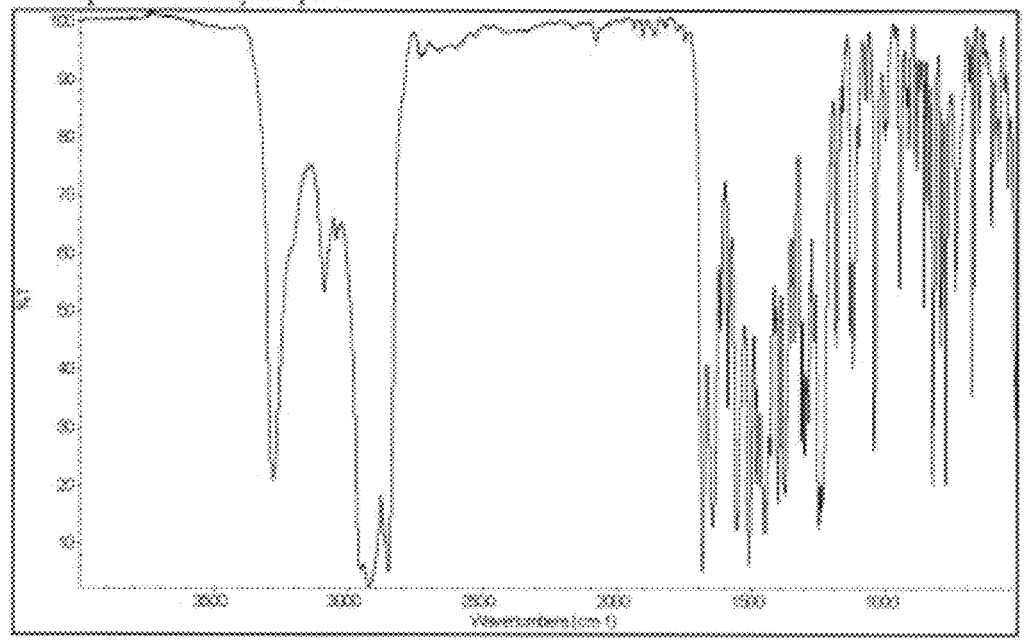
FIGS. 2 and 11: IR spectra of polymorph A of a compound of formula 1 (method Nujol Mull).
Figure 2:
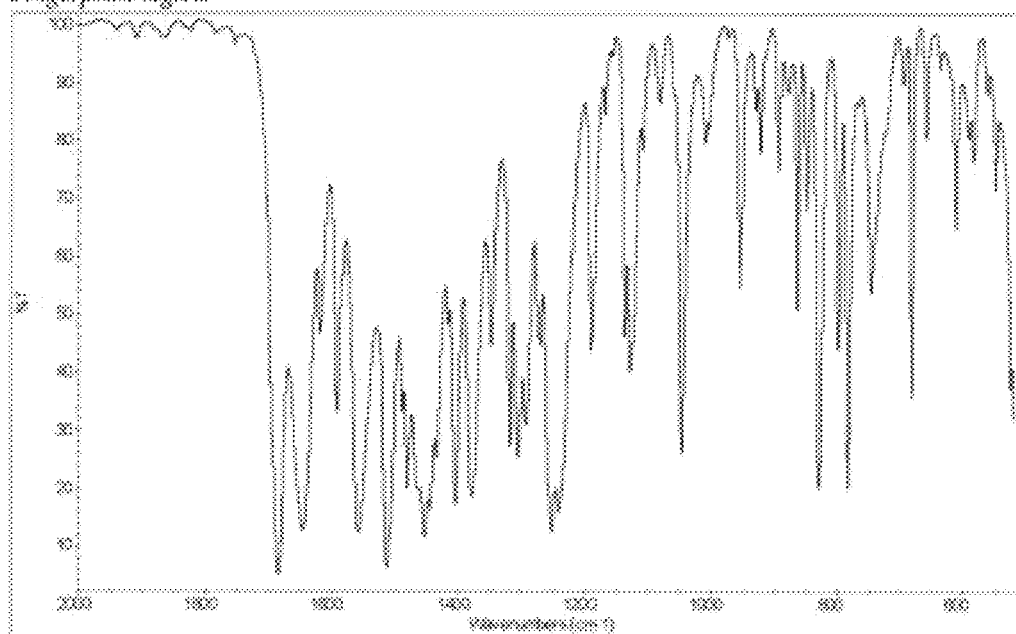

A certain embodiment of the invention relates to the crystalline polymorph A of the compound of formula 1 as described herein, characterized by the infrared spectrum shown in FIG. 2.

Figure 3:
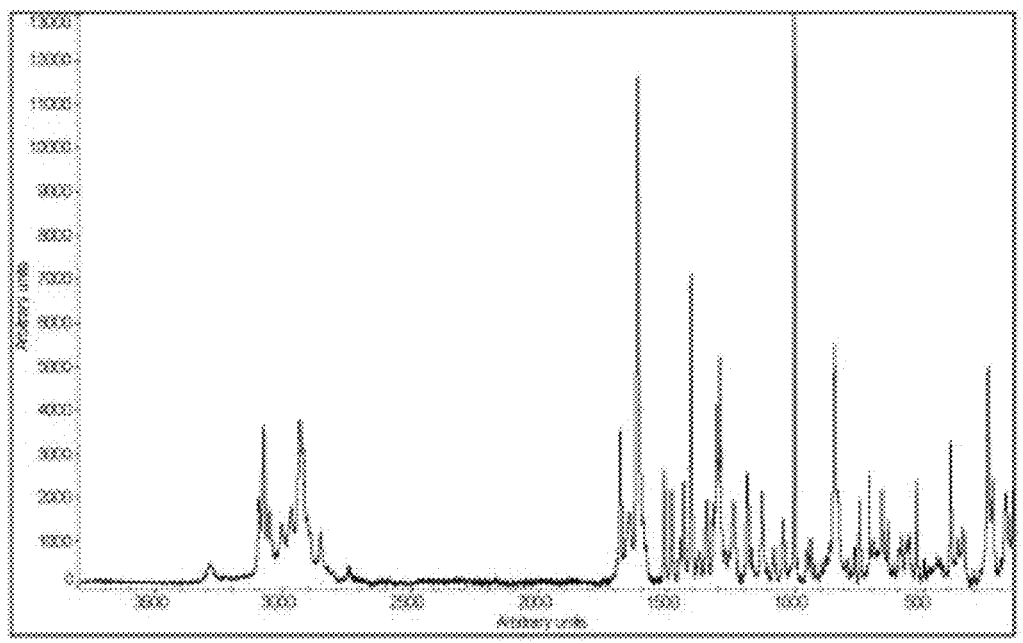
FIG. 3: Raman spectra of polymorph A of a compound of formula 1 (excitation at 785 nm).
Figure 3:
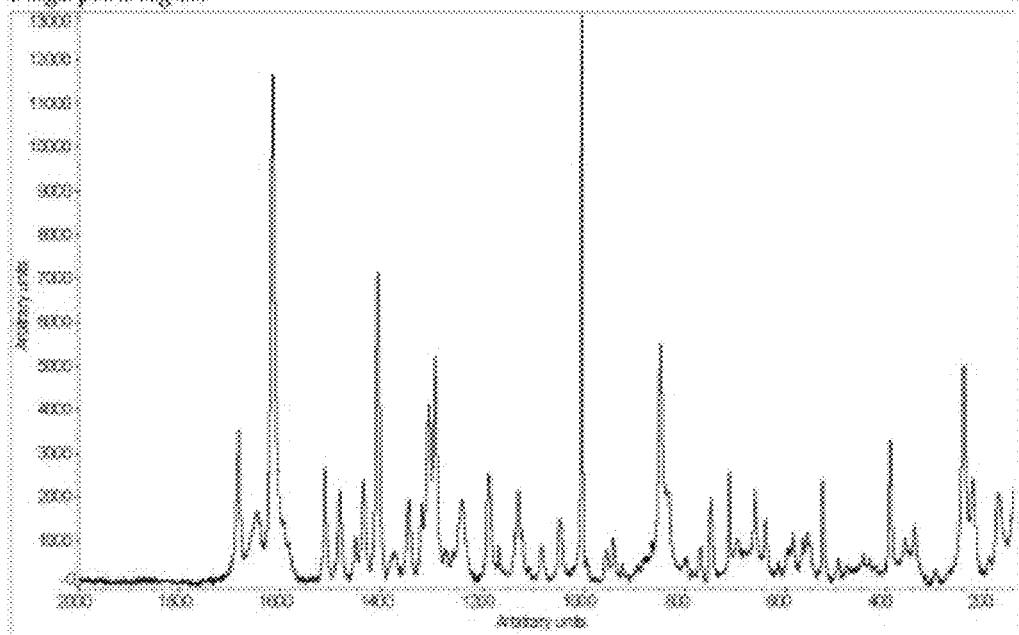

A certain embodiment of the invention relates to the crystalline polymorph A of the compound of formula 1 as described herein, characterized by the Raman spectrum shown in FIG. 3.

A certain embodiment of the invention relates to the crystalline polymorph A of the compound of formula 1 as described herein, characterized by the following unit cell parameters

| | |
|---|---|
| a | 4.96 |
| b | 11.22 |
| c | 30.32 |
| alpha | 90 deg |
| beta | 90 deg |
| gamma | 90 deg. |

Figure 5:
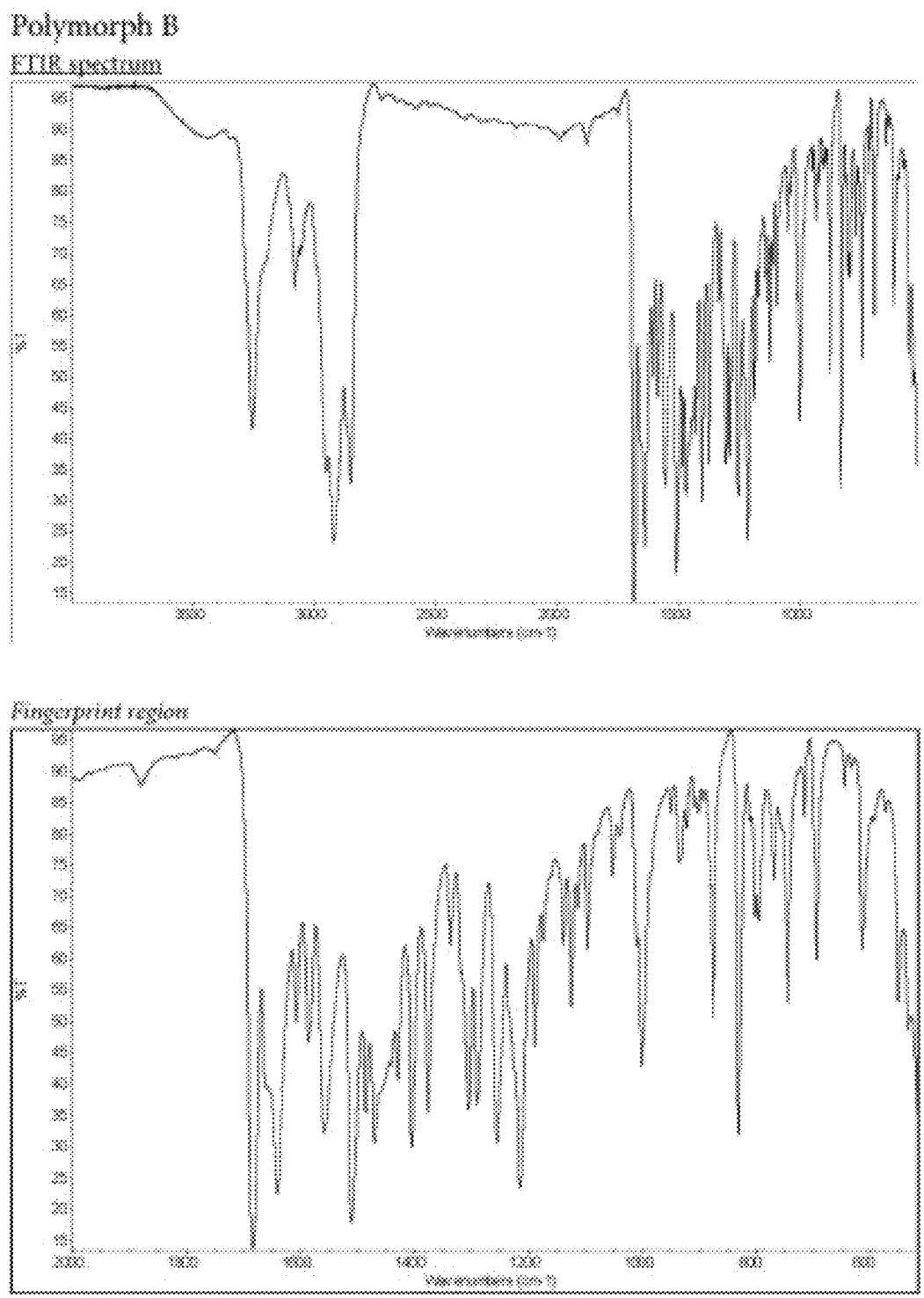
FIGS. 5 and 12: IR spectra of polymorph B of a compound of formula 1 (method Nujol Mull).

A certain embodiment of the invention relates to the crystalline polymorph B of the compound of formula 1 as described herein, characterized by the infrared spectrum shown in FIG. 5.

Figure 6:
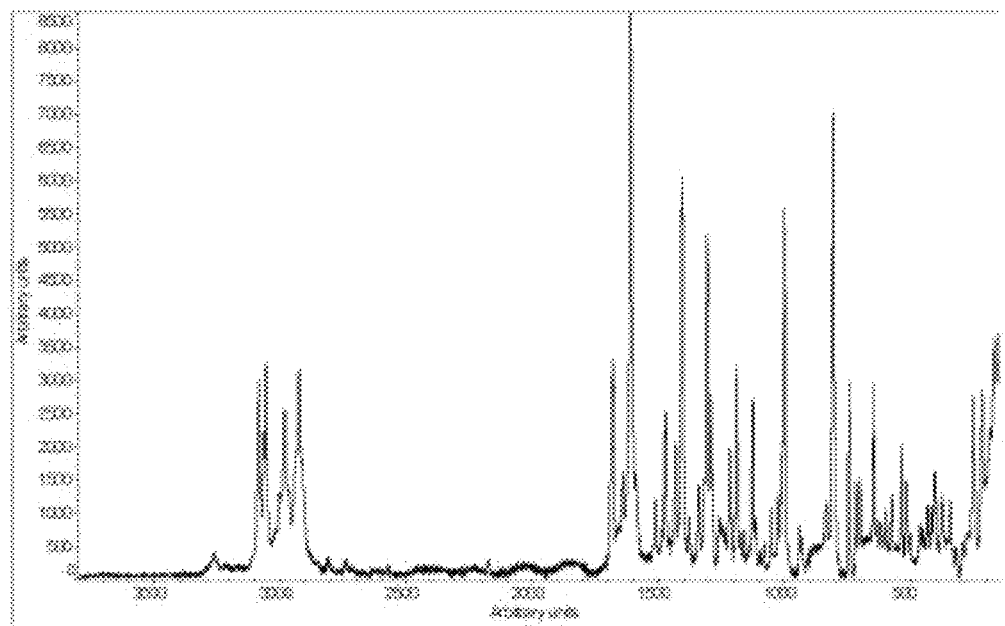
FIG. 6: Raman spectra of polymorph B of a compound of formula 1 (excitation at 633 nm).
Figure 6:
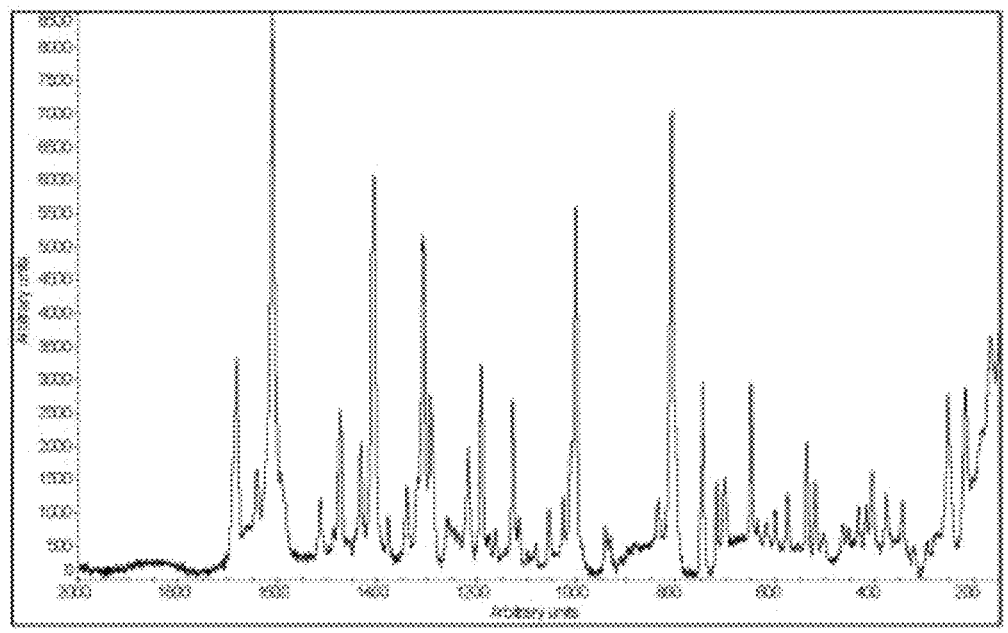

A certain embodiment of the invention relates to the crystalline polymorph B of the compound of formula 1 as described herein, characterized by the Raman spectrum shown in FIG. 6.

A certain embodiment of the invention relates to the crystalline polymorph B of the compound of formula 1 as described herein, characterized by the following unit cell parameters

| | |
|---|---|
| a | 9.63 |
| b | 12.39 |
| c | 13.49 |
| alpha | 90 deg |
| beta | 90 deg |
| gamma | 90 deg. |

A certain embodiment of the invention relates to the crystalline polymorph C of the compound of formula 1 as described herein, characterized by a X-ray powder diffraction pattern having the characteristic peaks expressed in values of degrees 2-theta at approximately

| degree 2-theta |
|---|
| 5.8 |
| 8.7 |
| 11.5 |
| 15.5 |
| 15.9 |
| 16.8 |
| 17.3 |
| 22.5 |
| 23.9. |

A certain embodiment of the invention relates to the crystalline polymorph C of the compound of formula 1 as described herein, characterized by a X-ray powder diffraction pattern having the characteristic peaks expressed in values of degrees 2-theta at approximately

| degree 2-theta |
|---|
| 5.8 |
| 8.7 |
| 15.5 |
| 15.9. |

Figure 7:
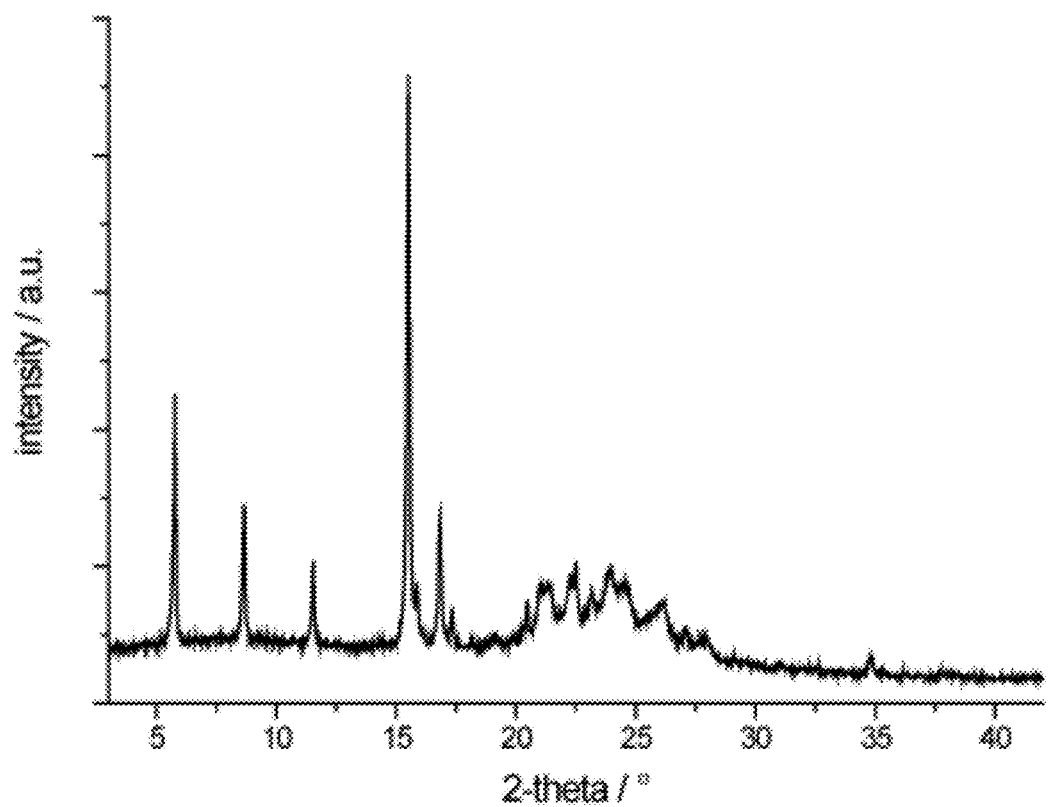
FIG. 7: XRPD pattern of polymorph C of a compound of formula 1.

A certain embodiment of the invention relates to the crystalline polymorph C of the compound of formula 1 as described herein, characterized by the X-ray powder diffraction pattern as shown in FIG. 7.

Figure 8:
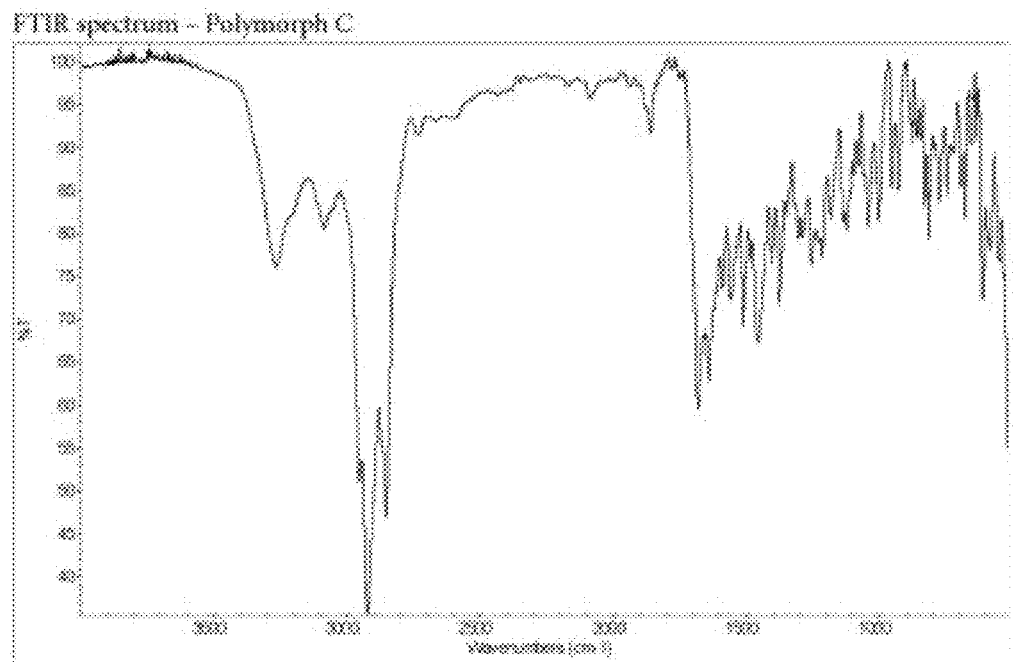
FIGS. 8 and 13: IR spectra of polymorph C of a compound of formula 1 (method Nujol Mull).
Figure 8:
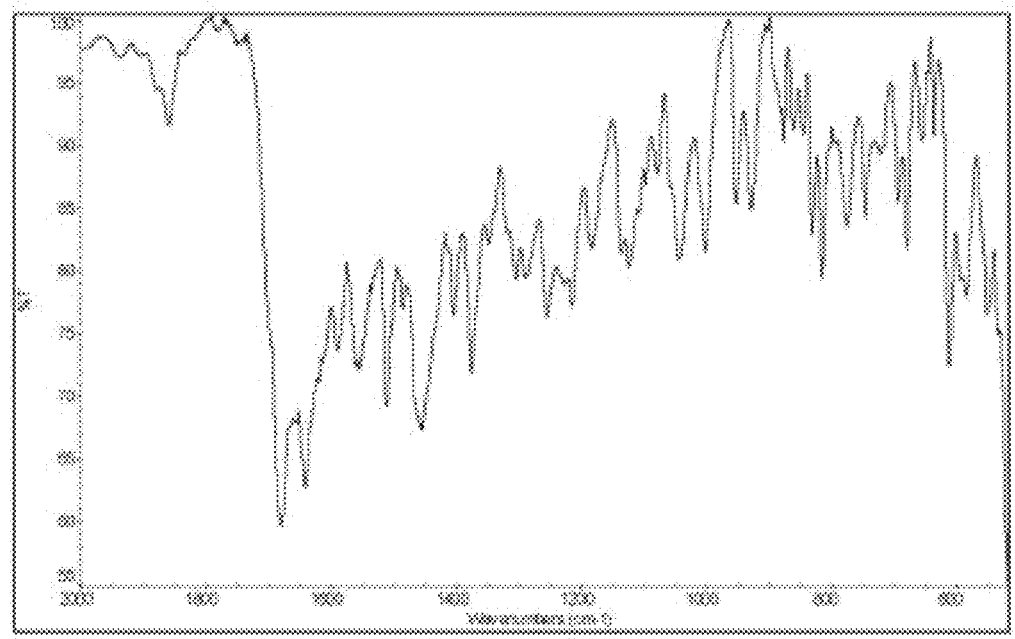

A certain embodiment of the invention relates to the crystalline polymorph C of the compound of formula 1 as described herein, characterized by the infrared spectrum shown in FIG. 8.

Figure 9:
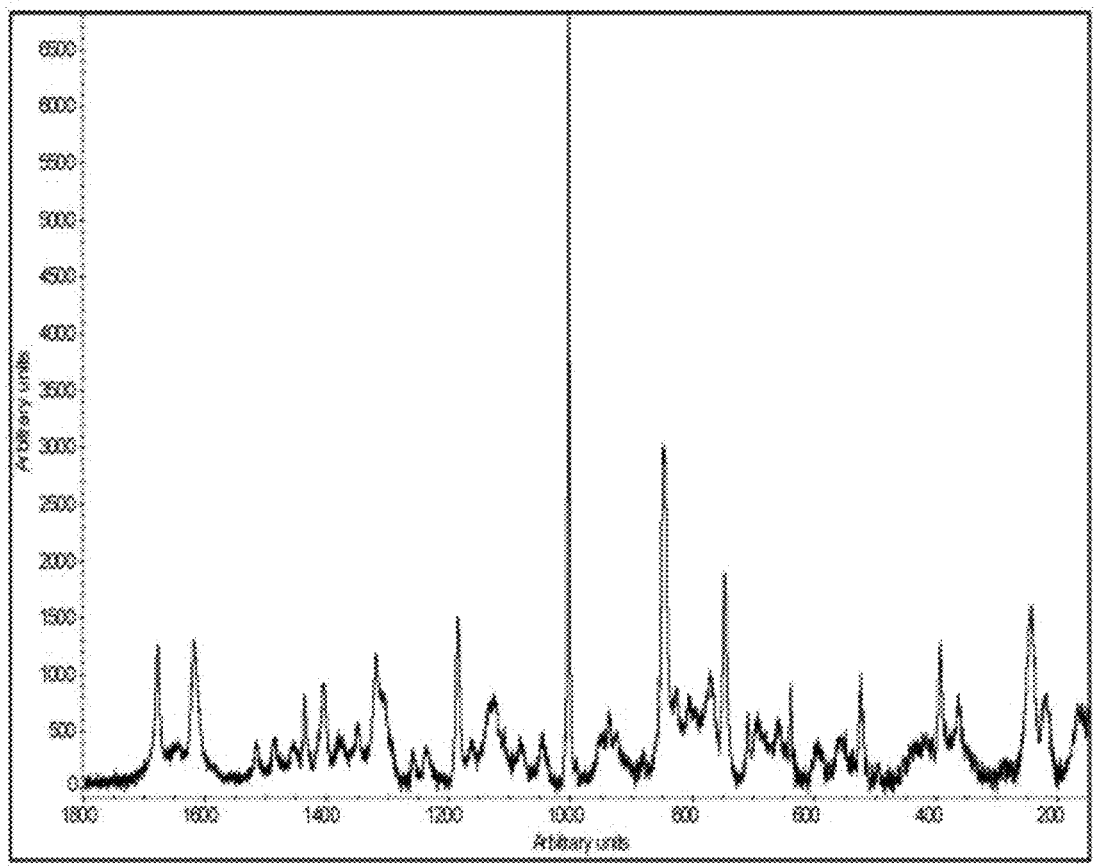
FIG. 9: Raman spectrum of polymorph C of a compound of formula 1 (excitation at 785 nm).

A certain embodiment of the invention relates to the crystalline polymorph C of the compound of formula 1 as described herein, characterized by the Raman spectrum shown in FIG. 9.

Figure 10:
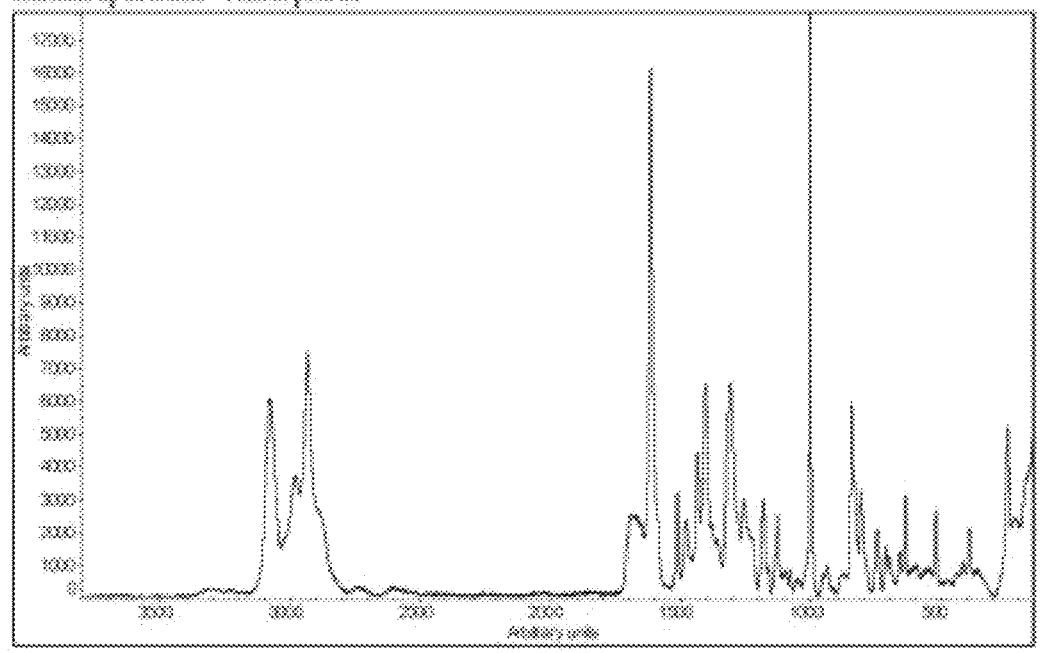
FIG. 10: Raman spectra of amorphous compound of formula 1 (excitation at 633 nm).
In figures of Raman spectra, where the "x" axes are labeled 'arbitrary units' the axis is in units of "wavenumbers $cm^{-1}$".
Figure 10:
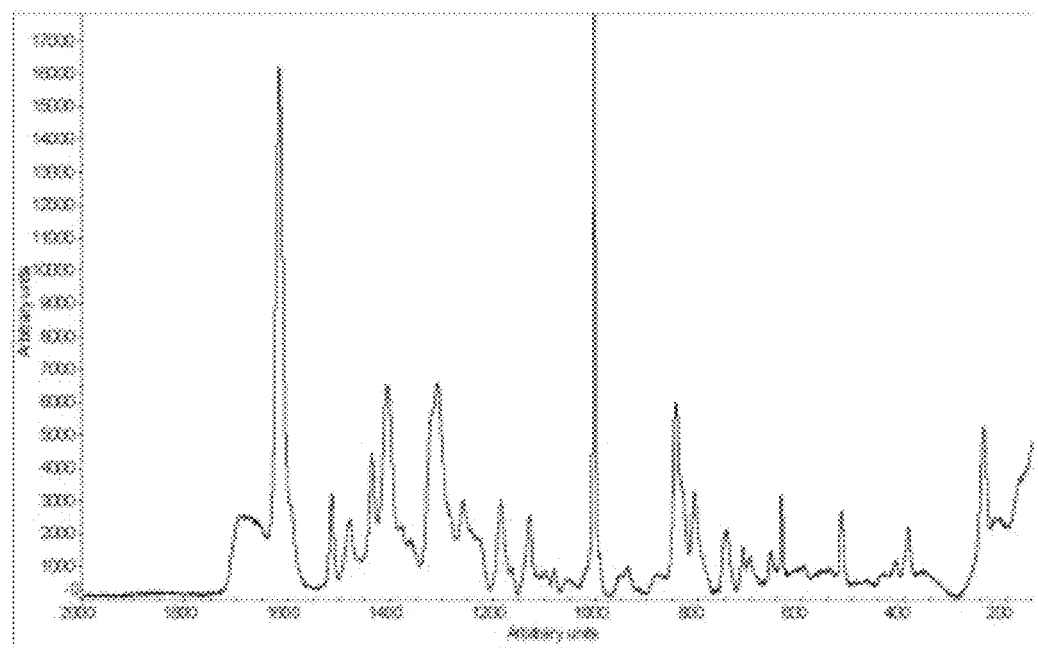
Figure 11:
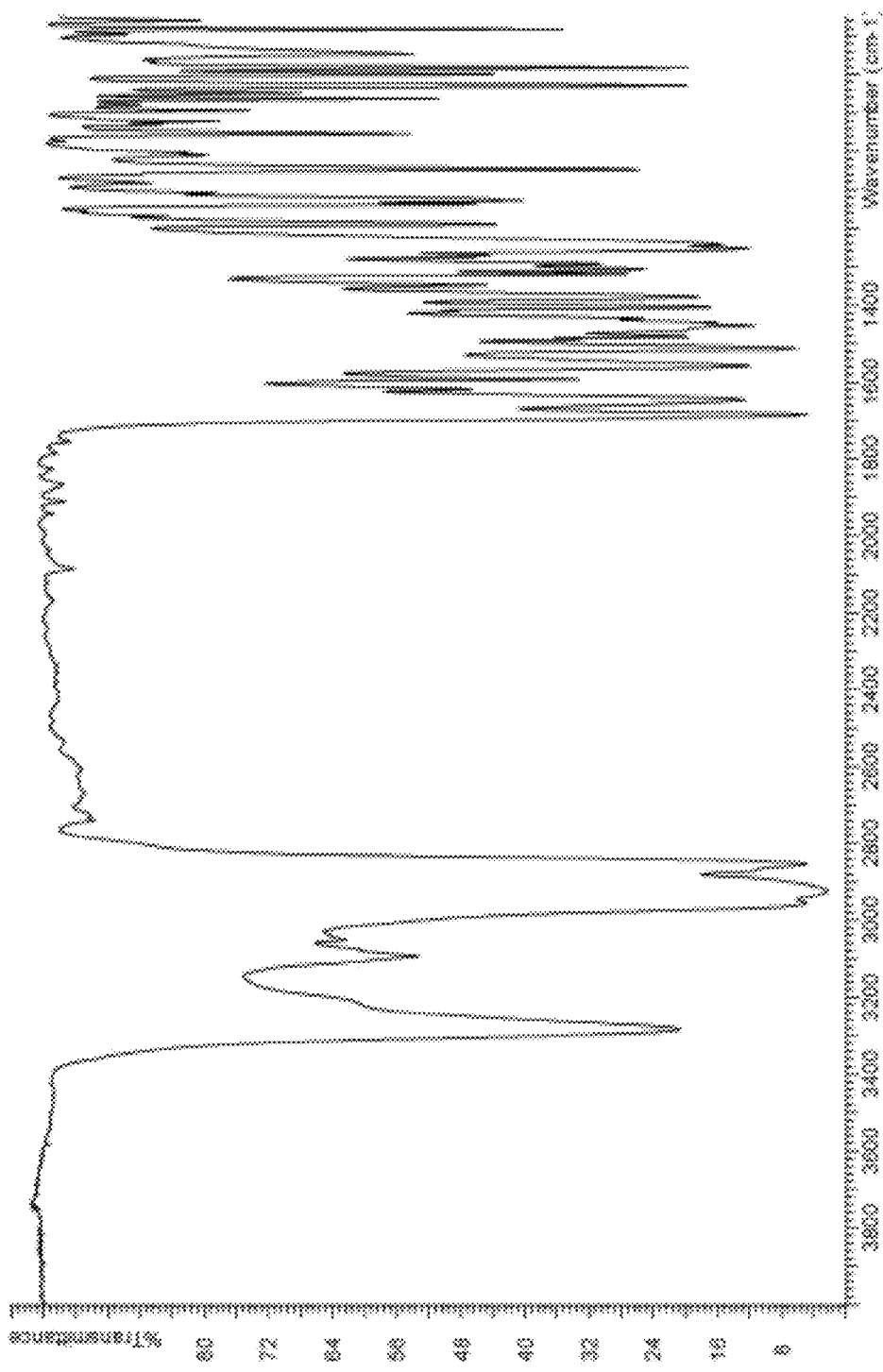
Figure 12:
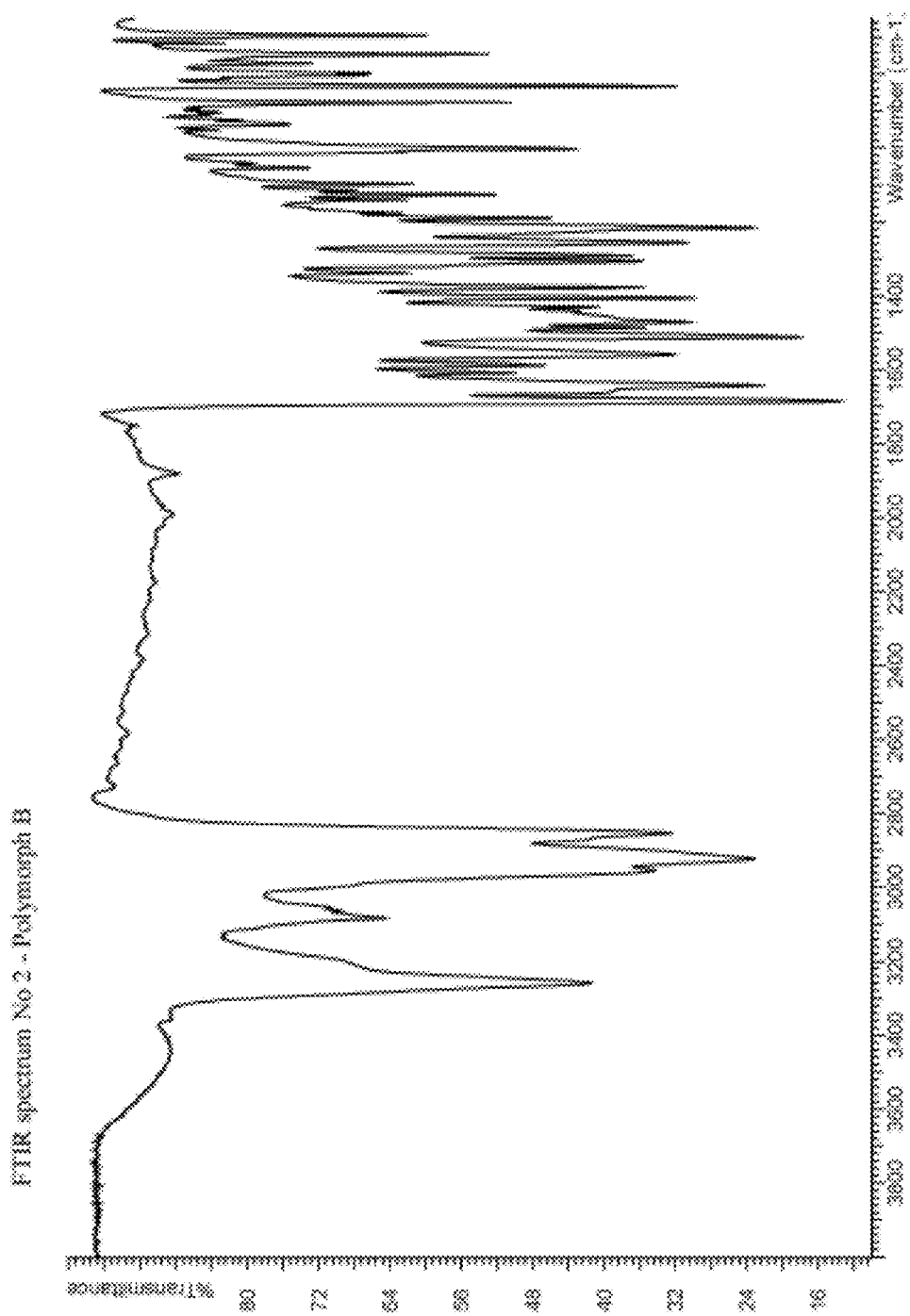
Figure 13:
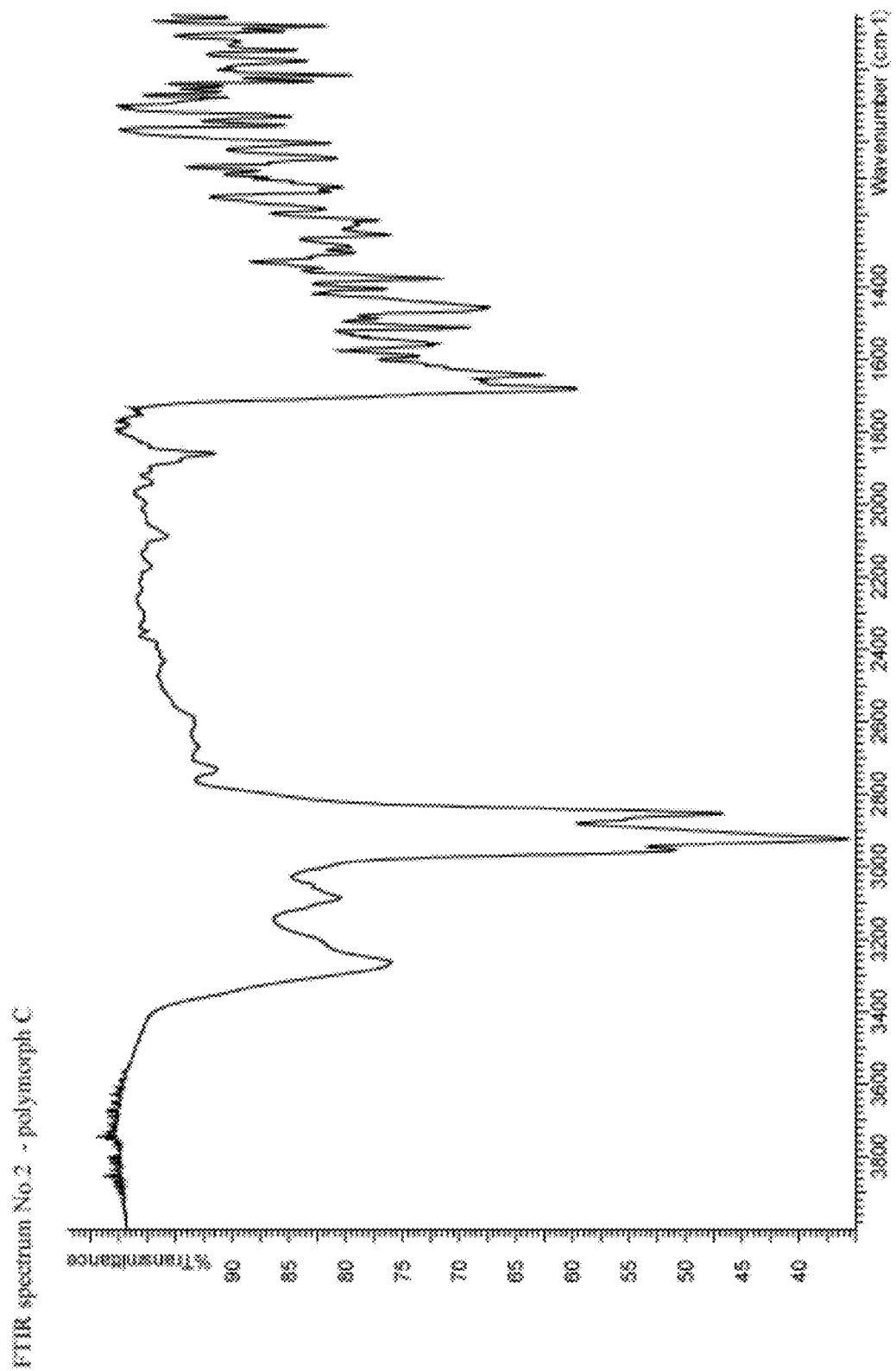

A certain embodiment of the invention relates to the amorphous form of the compound of formula 1 as described herein, characterized by the Raman spectrum shown in FIG. 10.

EXPERIMENTAL

The following experiments are provided for illustration of the invention. They should not be considered as limiting the scope of the invention, but merely as being representative thereof.

Polymorph A

Crude 1 was dissolved in acetonitrile/water 80:20 at 65° C. Cooling to 22° C. within 8 h afforded crystals of Polymorph A.

Polymorph B 240 mg of crude 1 were re-crystallized in 10 mL of 2-butanone by cooling crystallization to ambient temperature, yielding 167 mg of Polymorph B crystals. Polymorph B is the thermodynamically stable form at room temperature. Polymorph B is the thermodynamic most stable form at room temperature.

Polymorph C 100 mg of 1 were incubated at 200° C. on a heating plate. After obtaining a complete melt, the sample was cooled to ambient temperature and analyzed immediately.

Amorphous 1

50 mg of 1 were incubated at 200° C. on a heating plate. After obtaining a complete melt, the sample was rapidly cooled to ambient temperature and analyzed immediately (see FIG. 10).

(S)-3-Acetylamino-γ-butyrolactone (3)

To a stirred suspension of (S)-3-amino-γ-butyrolactone hydrochloride (2) (55.0 g, 400 mmol, Sinochem) in acetone (800 ml) were added at room temperature acetic anhydride (40.8 g, 400 mmol) and after stirring for 10 min potassium carbonate (111 g, 800 mmol) was added all at once. The reaction mixture was stirred at 20° C. for 3.5 h and the white suspension was filtered and the inorganic salt residue was washed with acetone (~300 ml). Evaporation of the filtrate (35-45° C./≥10 mbar) afforded 60.5 g (106%) crude, crystalline residue, which was dissolved in isopropyl acetate (1150 ml) at ca. 90° C. The slightly turbid solution was filtered and the clear filtrate cooled down and stirred at room temperature for 18 h and at 0° C. for 3 h. Filtration of the resulting suspension gave after washing with cold isobutyl acetate (~100 ml) and drying (55° C./10 mbar/6 h) 48.3 g (84.4%) product (3) as white crystalline powder, mp. 121-125° C. (99.0% ee). $[\alpha]_D^{20}$=−137.0 ($CHCl_3$; c=1.0). $^1H$ NMR (400 MHz, $CDCl_3$) δ 2.01 (s, 3H), 2.47 & 2.86 (ABX, $J_{AB}$=18.0 Hz, $J_{AX}$=2.4 Hz, $J_{BX}$=8.1 Hz, each 1H), 4.27 & 4.51 (ABX, $J_{AB}$=9.9 Hz, $J_{AX}$=2.1 Hz, $J_{BX}$=5.6 Hz, each 1H), 4.71 (m, 1H), 6.70 (br s, J=1H). ESI-MS (m/z) 144 $[M+H]^+$, 166 $[M+Na]^+$.

4-(3-fluorobenzyloxy)aniline hydrochloride (5)

To a stirred solution of 4-aminophenol (4a) (32.7 g, 300 mmol, Aldrich) in dimethylformamide (400 ml) was added at 0° C. 168 g 20% potassium tert-butoxide in THF (168 g, 300 mmol, ACROS) over 0.5 h. To the dark brown suspension was added at 0° C. 3-fluorobenzyl chloride (4) (28.9 g, 200 mmol, ABCR) over 1 h and stirring at 0° C. was continued for 1.5 h. The reaction mixture was added to tert-butylmethyether (1000 ml) and washed sequentially with water (1000 ml), 0.1M NaOH (1000 ml) and water (1000 ml). The organic layer was dried ($Na_2SO_4$), filtered and the solvent was removed by rotary evaporation (35-45° C./≥10 mbar) affording 41.3 g (95.1%) crude product as a dark-brown oil, which was dissolved in ethyl acetate (800 ml). To the resulting dark-brown solution was added at room temperature 2 M HCl in ethanol (100 ml, 200 mmol) over 0.5 h and the resulting beige suspension was stirred for 2 h then filtered, washed with ethylacetate (3×50 ml) and dried (50° C./10 mbar/3 h) affording 45.6 g (89.8%) hydrochloride (5) as a beige, crystalline powder. $^1H$ NMR (400 MHz, DMSO-$d_6$) δ 6.16, (s, 2H), 7.09-7.50 (m, 8H), 10.25 (br s, 3H). ESI-MS (m/z) 218 $[M+H]^+$. Anal. Calcd. for $C_{13}H_{12}FNO$ HCl (253.71). C, 61.55; H, 5.16; N, 5.52; O, 6.31; Cl, 13.97; F, 7.49. Found. C, 61.26; H, 5.09; N, 5.45; O, 6.51; Cl, 13.92; F, 7.51.

(S)-3-Acetylamino-N-[4-(3-fluoro-benzyloxy)-phenyl]-4-hydroxy-butyramide (6)

To 4-(3-fluorobenzyloxy)aniline hydrochloride (5) (38.1 g, 150 mmol), 14.3 g(S)-3-acetylamino-γ-butyrolactone (3) (14.3 g, 100 mmol) and 33.2 g sodium 2-ethylhexanoate (200 mmol) was added toluene (200 ml). The dark-beige suspension was heated up to approx. 107° C. and stirred under reflux for 6 h (oil bath 120° C.; after stirring for ca. 1 h, thick, beige slurry was formed, which upon extended stirring thinned down). After cooling to ca. 95° C., water (200 ml) was added and the three-phase reaction mixture was further cooled down and stirred at rt. for 16 h. Filtration and washing with toluene (100 ml), water (100 ml) and toluene (100 ml) gave after drying (55° C./10 mbar/20 h) 32.6 g (90.5%) compound (6) as a white crystalline powder, mp. 194.5-196° C. (99.7% ee). $[\alpha]_D^{20}$=−7.75 (DMF; c=1). $^1H$ NMR (400 MHz, DMSO-$d_6$) δ 1.79 (s, 3H), 2.39 & 2.55 (ABX, $J_{AB}$=14.8 Hz, $J_{AX}$=7.5 Hz, $J_{BX}$=6.5 Hz, each 1H), 3.30-3.47 (m, 2H), 4.11 (m, 1H), 4.77 (t, J=5.5 Hz, 1H), 5.08 (s, 2H), 6.95 (d, J=9.1 Hz, 2H), 7.11-7.19 (m, 1H), 7.24-7.30 (m, 2H), 7.38-7.47 (m, 1H), 7.49 (d, J=9.1 Hz, 2H), 7.71 (d, J=8.1 Hz, 1H), 9.73 (s, 1H). ESI-MS (m/z) 361 $[M+H]^+$. Anal. Calcd. for $C_{19}H_{21}FN_2O_4$ (360.39). C, 63.32; H, 5.87; N, 7.77; O, 17.76; F, 5.27. Found. C, 63.30; H, 5.88; N, 7.61; O, 17.72; F, 5.23.

Alternatively, a suspension of 4-(3-fluorobenzyloxy)aniline hydrochloride (5) (55.0 g, 0.22 mol), (S)-3-acetylamino-γ-butyrolactone (3) (23.9 g, 0.17 mol) and sodium 2-ethylhexanoate (50.0 g, 0.30 mol) in toluene (330 ml) was heated up to approx. 86° C. and stirred at this temperature for 17 h. To the suspension was then added at 80° C. within 60 minutes water (435 ml) and the three-phase mixture was subsequently stirred at 80° C. for 60 minutes. The mixture was then cooled to down to 30° C. and subsequently stirred at this temperature for 2 h. Filtration and washing with toluene (175 ml), water (175 ml) and toluene (175 ml) afforded after drying (65° C./10 mbar/20 h) 57.2 g (95%) compound (6) as a white crystalline powder with an assay of 98.2% (w/w) and a purity of 99.9% (area) (by HPLC).

Alternatively, to a thick white suspension of (S) methyl 2-acetamido-4-[4-[(3-fluorophenyl)methoxy]anilino]-4-oxobutanoate (10) (3.88 g, 10 mmol) in tetrahydrofuran (20 ml) was added at 0° C. 4 M lithium borohydride in tetrahydrofuran (5.5 ml, 22 mmol) over 2 h. After stirring at 0° C. for 2 h the clear solution was carefully hydrolyzed with 22 ml 1 M HCl (vigorous evolution of $H_2$ occurred, pH 4-5). Water (30 ml) was added and the white suspension was heated to ca. 40° C. until a clear solution was formed, then cooled down and crystallized by stirring at room temperature for 18 h and at 0° C. for 3 h. Filtration and washing with 20 ml cold water gave after drying (55° C./10 mbar/18 h) 2.95 g (82%) of the title compound (6) as a white, crystalline powder, mp. 193-195° C. (ee>98%). $^1H$ NMR (400 MHz, DMSO-$d_6$) δ 1.79 (s, 3H), 2.39 & 2.55 (ABX, $J_{AB}$=14.8 Hz, $J_{AX}$=7.5 Hz, $J_{BX}$=6.5 Hz, each 1H), 3.30-3.47 (m, 2H), 4.11 (m, 1H), 4.77 (t, J=5.5 Hz, 1H), 5.08 (s, 2H), 6.95 (d, J=9.1 Hz, 2H), 7.11-7.19 (m, 1H), 7.24-7.30 (m, 2H), 7.38-7.47 (m, 1H), 7.49 (d, J=9.1 Hz, 2H), 7.71 (d, J=8.1 Hz, 1H), 9.73 (s, 1H). ESI-MS (m/z) 361 $[M+H]^+$.

(S)-3-Acetylamino-4-chloro-N-[4-(3-fluoro-benzyloxy)-phenyl]-4-]-butyramide (7)

To a stirred suspension of hydroxyamide (6) (32.4 g, 90 mmol) in ethyl acetate (450 ml) was added thionyl chloride (11.0 g, 93 mmol) all at once. The reaction mixture was first stirred at room temperature for 4 h and after warming to reflux temperature at ca. 75° C. for 18 h (during warming up as well as at reflux temperature, a moderate gas evolution of $SO_2$ and HCl was observed). The white suspension was cooled to, filtered and washed with ethyl acetate (250 ml) affording after drying (55° C./10 mbar/18 h) 32.3 g (94.7%) product (7) as a white crystalline powder. $^1H$ NMR (400 MHz, DMSO-$d_6$) δ ppm 1.82 (s, 3H), 2.55 & 2.70 (ABX, $J_{AB}$=15.3 Hz, $J_{AX}$=7.3 Hz, $J_{BX}$=6.4 Hz, each 1H), 3.70 & 3.77 (ABX, $J_{AB}$=11.0 Hz, $J_{AX}$=5.4 Hz, $J_{BX}$=4.8 Hz, each 1H), 4.32-4.42 (m, 1H), 5.09 (s, 1H), 6.95 (d, J=9.1 Hz, 2H), 7.10-7.20 (m, 2H), 7.23-7.30 (m, 2H), 7.38-7.47 (m, 1H), 7.49 (d, J=9.1 Hz, 2H), 7.71 (d, J=8.1 Hz, 1H), 9.73 (s, 1H). ESI-MS (m/z) 379 $[M+H]^+$, 401 $[M+Na]^+$. Anal. Calcd for $C_{19}H_{20}ClFN_2O_3$ (378.83): Calcd. C, 60.24; H, 5.32; N, 7.39; O, 12.67; Cl, 9.36; F, 5.02. Found C, 59.65; H, 5.25; N, 7.15; O, 12.67; Cl, 9.67; F, 5.03.

(S)—N-[1-[4-(3-fluoro-benzyloxy)-phenyl]-5-oxo-pyrrolidin-3-yl-]acetamide (1)

To a suspension of chloride (7) (37.9 g, 100 mmol) in 2-methyltetrahydrofurane (600 ml) was added under vigorous stirring at 0° C. 1.65 M potassium tert-butoxide in THF (75.5 ml, 125 mmol, ACROS) over 2.5 h. After additional stirring at 0° C. for 1 h, the cold suspension was hydrolyzed with 0.1 M HCl (600 ml) and the reaction mixture was stirred at 30° C. for 0.5 h. The organic layer was washed with water (300 ml), dried ($Na_2SO_4$) and filtered. Removal of the solvent by rotary evaporation (50° C./≥10 mbar) afforded 32.1 g crystalline residue, which was dissolved in 2-butanone (400 ml) at ca. 95° C. and hot filtered. Crystallization, which was induced by seeding and cooling to room temperature and 0° C. (4 h) afforded 25.4 g (74.2%) of the titled compound (1) as an off-white, crystalline powder, mp. 162-164° C. (polymorph B). Ee>99.8%, $[\alpha]_D^{20}$=−17.8 (DMF; c=1). $^1$H NMR (400 MHz, DMSO-$d_6$) δ ppm 1.82 (s, 3H), 2.34 (dd, $J_1$=17.1, $J_2$=3.9, 1H), 2.84 (dd, $J_1$=17.1, $J_2$=8.2, 1H), 3.55 (dd, $J_1$=10.2, $J_2$=3.2, 1H), 4.07 (dd, $J_1$=10.2, $J_2$=6.7, 1H), 4.32-4.41 (m, 1H), 5.13 (s, 2H), 7.02 & 7.55 (d, J=9.1, each 1H), 7.11-7.19 (m, 1H), 7.24-7.31 (m, 1H), 7.40-7.47 (m, 1H), 8.40 (d, J=6.4, 1H). ESI-MS (m/z) 343 [M+H]$^+$, 365 [M+Na]$^+$. Anal. Calcd for $C_{19}H_{19}FN_2O_3$ (342.37): Calcd. C, 66.66; H, 5.59; N, 8.18; F, 5.02; O, 14.02. Found C, 66.76; H, 5.48; N, 8.13; F, 5.03; O, 13.99.

Crystallized (1) form previous step (9.5 g, 0.028 mol) was dissolved in 2-butanone (290 mL) upon heating. The hot solution was filtered over charcoal. The solution was concentrated by removal of 2-butanone (200 mL) by distillation prior to seeded cooling crystallization. Filtration, washing with chilled 2-butanone and drying at 50° C./25 mbar/16 h afforded 9.18 g (93.9% corrected yield) of the title compound (1) as a crystalline powder of polymorphic form B with an assay of 100.4% (w/w) and a purity of 99.97% (area) (by HPLC).

Alternatively, to a stirred suspension of hydroxyamide (6) (30.0 g, 0.083 mol) in toluene (500 ml) was added at 50° C. within 45 minutes thionyl chloride (10.40 g, 0.087 mol) and the resulting mixture was stirred for 3 h at 50° C. The mixture was then heated up to 92° C. and subsequently stirred at this temperature for 15 h. The Suspension was then cooled to 50° C. and toluene was removed by distillation under reduced pressure. The distillation residue was cooled to ambient temperature and treated with N-methylpyrrolidone (210 ml) to obtain an almost clear solution. This solution was then cooled to −10° C. and subsequently treated at this temperature within 2 h with a solution of potassium tert-butoxide (12.40 g, 0.111 mol) in THF (60 g). The resulting mixture was stirred for another 60 minutes at −10° C., then warmed up to room temperature within 60 minutes and subsequently stirred at room temperature for 6 h. The reaction mixture was quenched with water (150 g) and the pH was adjusted with acetic acid (approx. 1.8 g) to pH 7-8. The mixture was then heated to 30-45° C. and THF and toluene were distilled off under reduced pressure (<200 mbar) to obtain a clear NMP/water mixture (400 ml). This mixture was heated to 45° C. and 260 mg of seed crystals were added. Water (320 ml) was then added within 3 h whereby the product crystallized. The resulting suspension was cooled to room temperature within 3 h and subsequently stirred at this temperature for 2 h. Filtration and washing of the filter cake with a mixture of water (100 ml) and N-methylpyrrolidone (20 ml) and subsequently only with water (150 ml) afforded after drying (70° C./10 mbar/20 h) 26.2 g (92%) of the title compound (1) as a crystalline powder with an assay of 99.6% (w/w) and a purity of 99.7% (area) (by HPLC).

3-acetamido-4-methoxy-4-oxo-butanoic acid (9)

N-α-Acetyl-L-aspartic acid α,β-dimethylester (50 g, 242 mmol, 1 eq.) was dissolved in 100 mM potassium phosphate buffer pH 6.0 (450 ml) under stirring. Lipase from *Candida antarctica* form B (CALB-L ex Novozymes; 5.0 ml) was added and the reaction mixture stirred at r.t. The pH was kept constant at 6.0 by the controlled addition of 1.0N NaOH (pH-stat). After 47 h and a consumption of 246.86 ml (247 mmol; 1.02 eq.) of NaOH solution the reaction was stopped by adjusting the pH to 2.1 (HCl 25%). The reaction mixture was saturated with sodium chloride (250 g) and extracted five times with 700 ml methyl-THF (first phase was quite cloudy (phase separation approx. 15 min.), the next phases were clear (<5 min. separation time). The combined organic phases were dried over sodium sulfate, evaporated and dried overnight at HV to give 45.24 g of a white solid which was recrystallized from 450 ml isopropyl acetate (1 h at 90° C., cooled slowly down to r.t.). The crystals (9) were filtered off, washed with ca. 25 ml isopropyl acetate and dried at HV (1 d) to give 37.94 g (82%) N-α-acetyl-L-aspartic acid α-methylester (99.5% HPLC, 98.5% ee (HPLC), MS(-ESI): 188.05 (M−H$^-$); $^1$H NMR (600 MHz, DMSO-d6): δ ppm 1.83 (s, 3H), 2.56-2.62 & 2.66-2.75 (dd each, 2H), 3.61 (s, 3H), 4.57 (td, J=7.6, 5.7 Hz, 1H), 8.32 (d, 1H), 12.44 (br s, 1H). $[\alpha]_D(20°$ C.)=−13.1° (c=5; EtOH).

Purity (HPLC): Column: XSelect Phenyl Hexyl×2, 150× 4.6 mm, 3.5 um. Starting Pressure: 226 bar; temp.: 50° C. Inj. vol.: 2.0 μL+wash. Flow: 1.0 ml/min. Det.: 204 nm. A: Water+5% ACN, 77-2% in 7 min., hold for 1 min.; B: 0.1% HCOOH, 18% isocratic; C: MeOH, 5-80% in 7 min., hold for 1 min. Sample prep.: 2 mg/ml ACN. Retention times: β-acid 5.93 min., diacid 6.18 min., α-acid 6.89 min., diester 6.96 min.

ee determination(HPLC): Column: Chiralpak IA-3 100× 4.6 mm, 3 um; 91 bar, 2 ml/min; temp.: 30° C. Ink vol.: 10.0 μL. Det.: 206 nm. A: n-heptane, 80%; B: EtOH, 20%. Sample prep.: 4 mg/ml EtOH. Retention times: D-enantiomer 2.21 min., L-enantiomer 2.71 min

(S) methyl 2-acetamido-4-[4-[(3-fluorophenyl)methoxy]anilino]-4-oxobutanoate (10)

A preformed solution of (S)-3-acetamido-4-methoxy-4-oxobutanoic acid (9) (3.78 g, 20 mmol) and 4-methylmorpholine (2.12 g, 21 mmol) in 20 ml acetonitrile (20 ml) was added at −10° C. over 1 h to solution of isobutyl chloroformate (2.73 g, 20 mmol) in acetonitrile (50 ml) and stirring at −10° C. was continued for 0.5 h. After the addition of 4-(3-Fluorobenzyloxy)aniline hydrochloride (5) (5.07 g, 20 mmol) 4-methylmorpholine (2.43 g, 24 mmol) was added at −10° C. over 1 h (a white suspension was formed) and stirring at −10° C. was continued for 1 h. The reaction mixture was warmed up to room temperature, hydrolyzed with 50 ml water and stirred overnight. The crystal suspension was filtered, washed with water (20 ml) and dried (55° C./10 mbar/18 h) affording 6.58 g (84.7%) product (10) as a white, crystalline powder, mp. 167-170° C., $[\alpha]_D^{20}$=−7.0 (DMF; c=1). $^1$H NMR (400 MHz, DMSO-$d_6$) δ 1.84 (s, 3H), 2.70 & 2.78 (ABX, $J_{AB}$=15.6 Hz, $J_{AX}$=7.0 Hz, $J_{BX}$=5.9 Hz, each 1H), 3.61 (s, 3H), 4.64 (q, J≈7.0 Hz, 1H), 5.09 (s, 2H), 6.95 (d, J=9.1 Hz, 2H), 7.11-7.19 (m, 1H), 7.24-7.30 (m, 2H), 7.38-7.47 (m, 1H), 7.48 (d, J=9.1 Hz, 2H), 8.32 (d, J=7.5 Hz, 1H), 9.87 (s, 1H). ESI-MS (m/z) 389.3 [M+H]$^+$ Anal. Calcd. for $C_{20}H_{21}FN_2O_5$ (388.40). Calcd: C, 61.85; H, 5.45; F, 4.89; N, 7.21; O, 20.60. Found: C, 61.81; H, 5.53; F, 4.89; N, 7.11; O, 20.63.

(S)-3-Acetylamino-γ-butyrolactone (3)

L-Aspartic anhydride, N-carboxy, tert-butyl ester (L-Boc-Aspartic anhydride)

In a reactor containing NaOH 15% (1105 g) is added portion-wise keeping temperature below 30° C. L-aspartic acid (260 g). Afterwards the mixture is diluted with methanol (351 mL) and warmed at 30-35° C. At this temperature a solution of di-tert-butyl dicarbonate (511 g) in methanol (204 mL) is added while keeping pH between 9.3 and 9.5 by addition of NaOH 30% (326 mL) and temperature between 30 and 35° C. After 3 h ethyl acetate (1560 mL) is added, the mixture is cooled down at 5° C. and hydrochloric acid 32.5% (595 mL) is added (the temperature is kept below 10° C.) to bring the pH to 3.0-3.5. At room temperature the aqueous phase is drained and extracted with ethyl acetate. The combined organic layers are washed with brine, then the solvents are rotary evaporated. The residue is taken up in toluene (650 mL) and water is removed by azeotropic distillation under vacuum. After addition of acetic anhydride (229 mL; 1.23 eq) over 30 minutes at 25-30° C. the mixture is stirred for additional 1 h. The mixture is then warmed at 30-35° C. and stirred for 5-10 hs. After cooling to room temperature, n-heptane (1825 mL) is added and a precipitate is formed which is stirred for 2 h at 10° C. and then filtered off. The wet cake is washed with n-heptane and dried under vacuum at 40° C. to give the desired product L-Boc-Aspartic anhydride as a white solid (348.9 g, 83% yield). Typical $^1$H-NMR signals (DMSO-d$_6$) at 1.40 ppm (s, 9H), 2.82 ppm (dd, 1H), 3.20 ppm (dd, 1H), 4.60 ppm (m, 1H), 7.75 (d, NH-Boc).

Carbamic acid, [(3S)-tetrahydro-5-oxo-3-furanyl]-1, 1-dimethylethyl ester (Boc-(S)-3-amino-γ-butyrolactone)

d$_6$) for the 3S isomer at 2.80 ppm (dd, 1H) and 7.45 ppm (bs, e-Boc), for the 2S isomer at 2.15 ppm (m, 1H) and 7.35 ppm (d, NH-Boc).

(4S)-2(3H)-Furanone, 4-aminodihydro-, hydrochloride ((S)-3-amino-γ-butyrolactone hydrochloride)

A reactor containing a suspension of boc-(S)-3-amino-γ-butyrolactone (114 g; 0.544 mmol) in 250 mL of isopropyl acetate is stirred at 20-25° C. for 30 min. Then a solution of HCl in isopropyl acetate (480 mL; 1.63 mmol) was added dropwise whereas the temperature is controlled. At the end of the addition the mixture is stirred over night at ca. 25° C. Finally the solid is filtered off, washed with isopropyl acetate and dried under vacuum to afford 74.2 g of (S)-3-amino-γ-butyrolactone hydrochloride with 100% purity and 99.1% yield. It consists of a 80:20 mixture of the two regioisomers 3S- and 2S- of the product (3). Typical $^1$H-NMR signals (DMSO-d$_6$) at 2.35 ppm (m, for 2S isomer), 2.60 ppm (dd, 1H), 3.0 ppm (dd, 1H) 8.8 ppm (bs, NH-Boc).

Alternatively, in a 2 L and 4-necked reactor under nitrogen 74.2 g of (S)-3-amino-γ-butyrolactone hydrochloride (0.539 moles) are suspended in acetone (880 g). The resulting suspension is stirred at 20-25° C. for 30 min, then acetic anhydride 55.1 g (0.539 moles) are added drop wise followed by portion-wise addition at ca. 5° C. of 150.4 g of potassium carbonate. The reaction mixture is stirred for 2 h at 0-5° C. until the conversion is complete. Afterwards the reaction is warmed over 1 h at 20-25° C., salts are filtered off and washed with acetone. The filtrate is rotary evaporated to dryness under vacuum, then 1.5 L of isopropyl acetate are added and the suspension is heated until it becomes a slightly turbid solution (70-75° C.). After filtration through a pad of celite the filtrate is cooled down slowly to 10-15° C. in 1 h, the resulting suspension is stirred for 2 h at this temperature, filtered and the filter cake is washed with isopropyl acetate to afford after drying 42.9 g of the desired product (3) (59% yield, 99% purity, <1% of 2S regioisomer).

We claim:

1. A crystalline form (polymorph A) of a compound of formula 1 characterized by an X-Ray

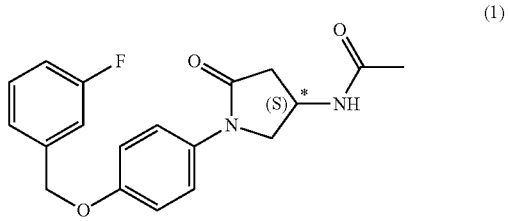

(1)

Powder Diffraction Pattern (XRPD) having characteristic peaks expressed in values of degrees 2-theta at approximately 8.4, 15.8, 16.9, 22.9 and 24.5.

2. A crystalline polymorph A according to claim 1 characterized by an XRPD having characteristic peaks expressed in values of degrees 2-theta at approximately

| degree 2-theta |
| --- |
| 5.8 |
| 8.4 |
| 9.8 |
| 11.7 |
| 14.1 |
| 15.8 |
| 16.9 |
| 19.8 |
| 20.4 |
| 21.5 |
| 22.0 |
| 22.9 |
| 24.5 |
| 26.4 |
| 28.2. |

3. A crystalline polymorph A according to claim 1 characterized by an XRPD as shown in FIG. 1.

4. A crystalline form (polymorph B) of a compound of formula 1 characterized by an XRPD having characteristic peaks expressed in values of degrees 2-theta at approximately 15.9, 21.3, 23.6 and 26.7.

5. A crystalline polymorph B according to claim 4 characterized by an XRPD having characteristic peaks expressed in values of degrees 2-theta at approximately

| degree 2-theta |
| --- |
| 11.6 |
| 13.3 |
| 15.9 |
| 16.9 |
| 18.1 |
| 19.7 |
| 20.7 |
| 21.3 |
| 22.5 |
| 23.6 |
| 24.1 |
| 26.7 |
| 27.8 |
| 29.0 |

6. A crystalline polymorph B according to claim 4 characterized by an XRPD as shown in FIG. 4.

7. A process to synthesize a compound according to claim 1 comprising the intramolecular cyclization of

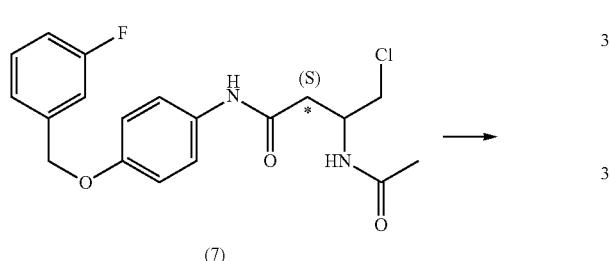

(7)

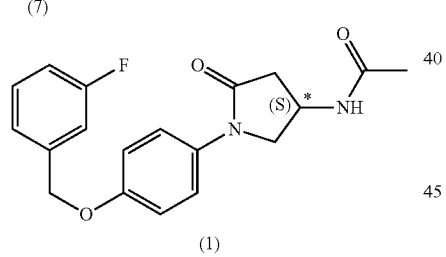

(1)

7 to afford 1.

8. A process according to claim 7 comprising the steps of:
(a) treating 3-acetamido-N-(4-((3-fluorobenzyl)oxy)phenyl)-4-hydroxybutanamide (6) with a chlorinating agent to afford 7

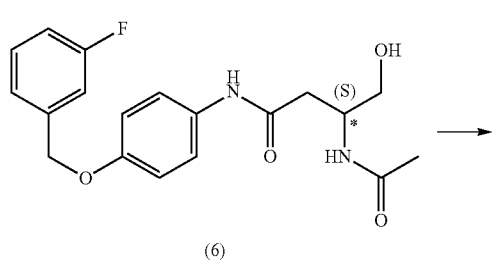

(6)

-continued

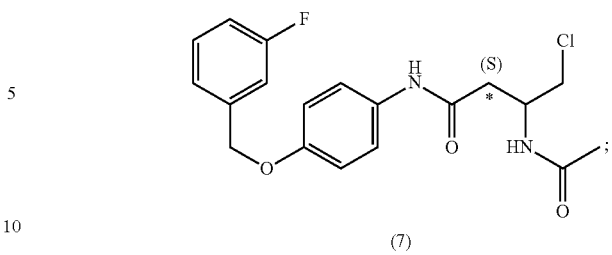

(7)

and,
(b) cyclizing 7 to afford 1

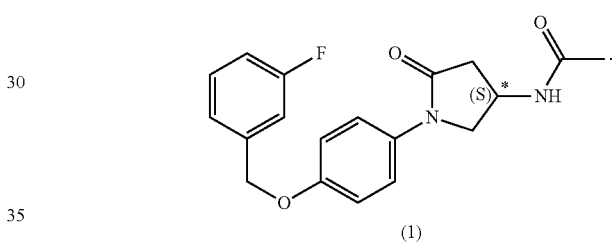

(7)

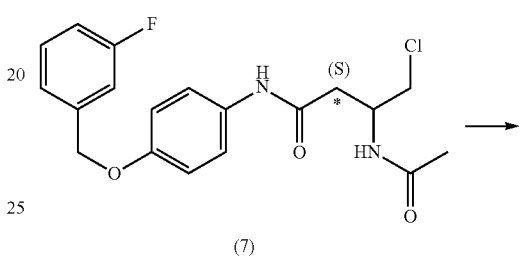

(1)

9. A process according to claim 8 wherein the chlorination step and the intramolecular cyclization step is

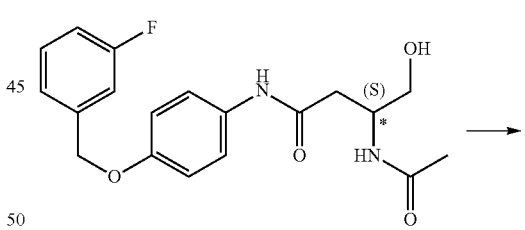

(6)

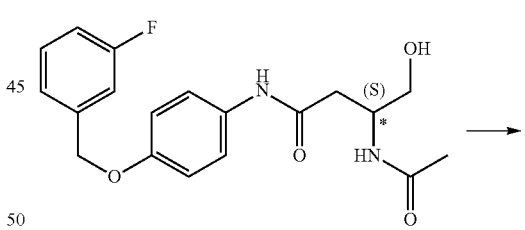

(7)

-continued

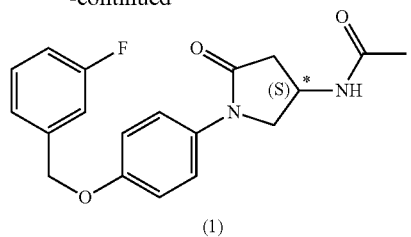

(1)

carried out as a one-pot reaction.

10. A process according to claim 7 comprising the steps of:
(a) treating (S)—N-(5-oxotetrahydrofuran-3-yl)acetamide (3) with 4-((3-fluorobenzyl)oxy)benzenaminium chloride (5) to afford 6

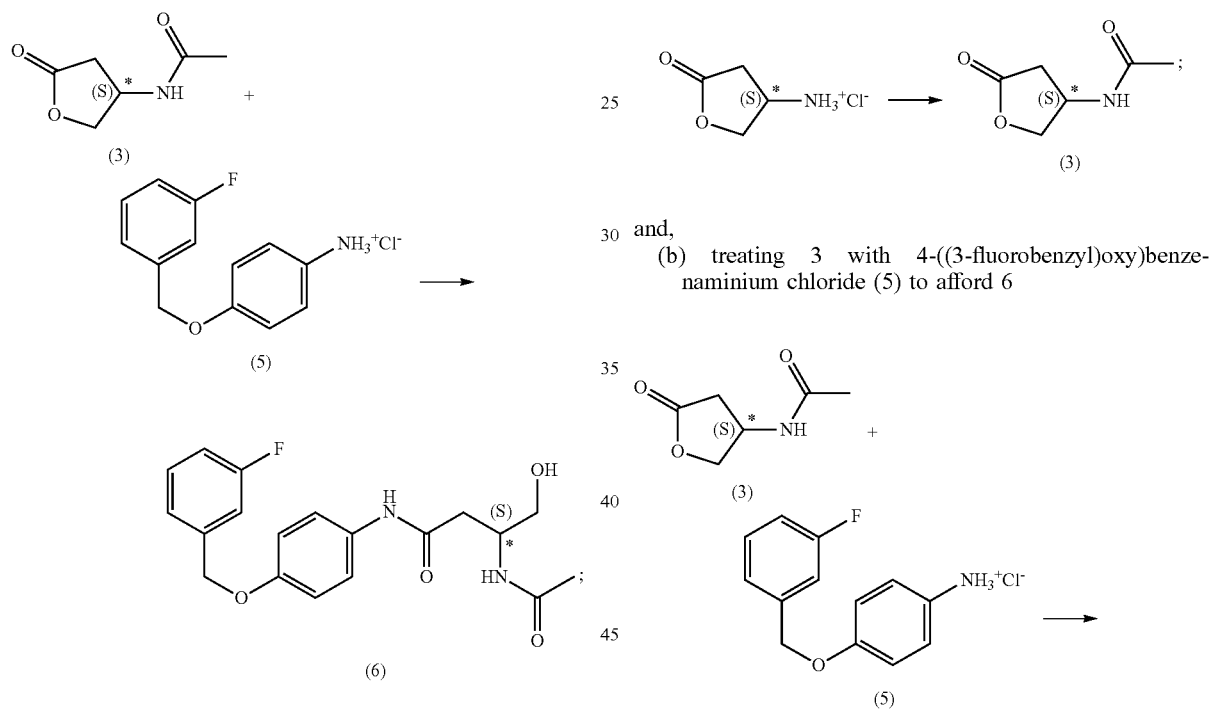

and,
(b) treating 6 with a chlorinating agent to afford (S)-3-acetamido-N-(4-((3-fluorobenzyl)oxy)phenyl)-4-hydroxybutanamide (7)

and,
(c) cyclizing 7 to afford 1

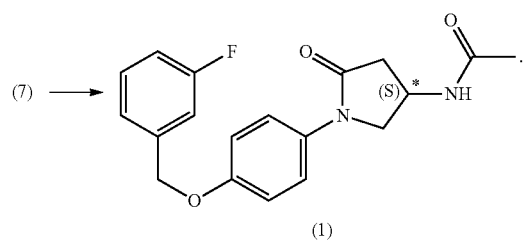

11. A process according to claim 7 comprising the steps of:
(a) treating (S)-5-oxotetrahydrofuran-3-aminium chloride with an acetylating agent to afford (S)—N-(5-oxotetrahydrofuran-3-yl)acetamide (3)

and,
(b) treating 3 with 4-((3-fluorobenzyl)oxy)benzenaminium chloride (5) to afford 6

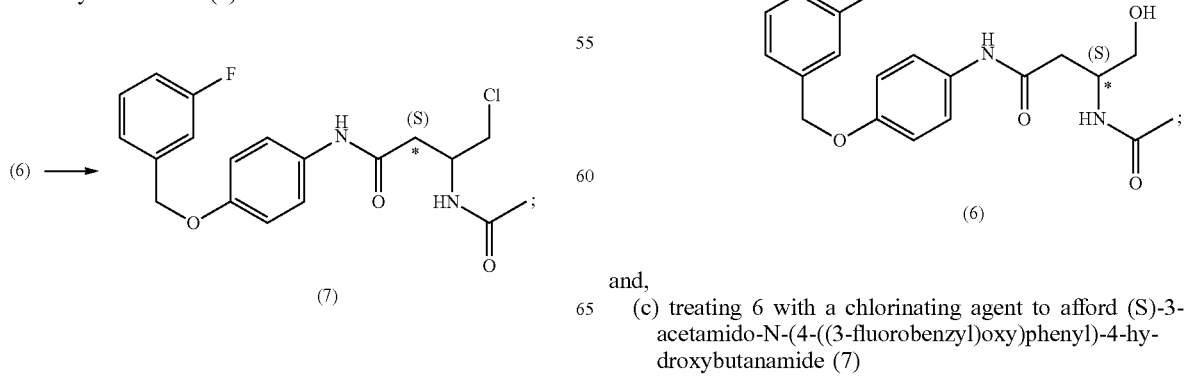

and,
(c) treating 6 with a chlorinating agent to afford (S)-3-acetamido-N-(4-((3-fluorobenzyl)oxy)phenyl)-4-hydroxybutanamide (7)

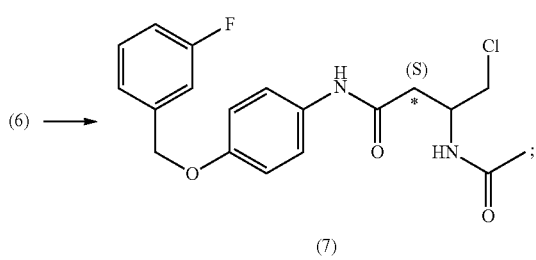

and,
(d) cyclizing 7 to afford 1

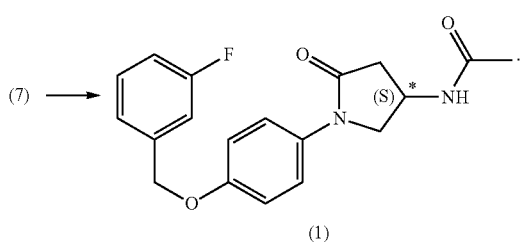

12. A process according to claim 7 which process further comprises the step of:
(a) reacting 3-fluorobenzyl chloride (4) and 4-hydroxy aniline (4a) to afford 4-((3-fluorobenzyl)oxy)benzenaminium chloride (5); (b) treating (S)-5-oxotetrahydrofuran-3-aminium chloride with an acetylating agent to afford (S)—N-(5-oxotetrahydrofuran-3-yl)acetamide (3), (c) treating 3 with 4-((3-fluorobenzyl)oxy) benzenaminium chloride (5) to afford 6; (d) treating 6 with a chlorinating agent to afford (S)-3-acetamido-N-(4-((3-fluorobenzyl)oxy)phenyl)-4-hydroxybutanamide (7); (e) cyclizing 7 to afford 1.

13. A process according to claim 8 comprising the steps of:

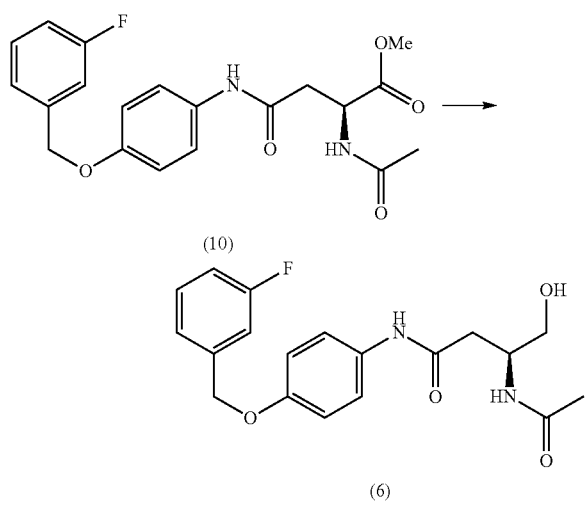

(a) reducing 2-acetamido-4-((4-((3-fluorobenzyl)oxy) phenyl)amino)-4-oxobutanoic acid (10) to afford (S)-3-acetamido-N-(4-((3-fluorobenzyl)oxy)phenyl)-4-hydroxybutanamide (6); (b) chlorinating 6; and (c) cyclizing 6 to afford 1.

14. A process according to claim 13 which process further comprises the step of:
(a) condensing (S)-3-acetamido-4-methoxy-4-oxobutanoic acid (9) and 5 to afford 10

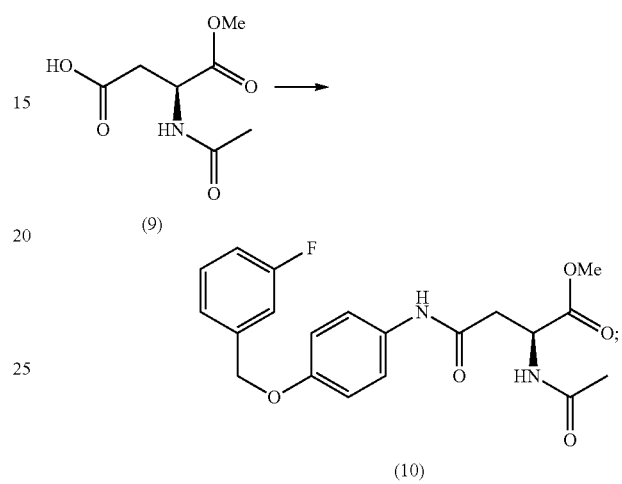

and,
(b) reducing 2-acetamido-4-((4-((3-fluorobenzyl)oxy) phenyl)amino)-4-oxobutanoic acid (10) to afford (S)-3-acetamido-N-(4-((3-fluorobenzyl)oxy)phenyl)-4-hydroxybutanamide (6); (c) chlorinating 6; and (d) cyclizing 6 to afford 1.

15. A process according to claim 13 which process further comprises the step of:
(a) selectively hydrolyzing (S)-dimethyl 2-acetamidosuccinate (8) to afford 9

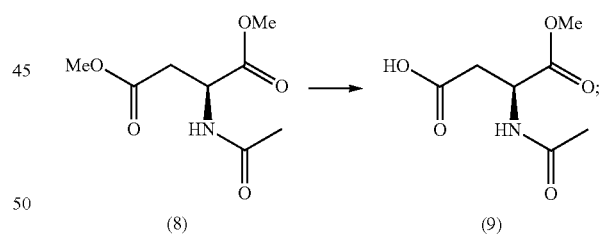

and,
(b) condensing 9 and 5 to afford 10; (c) reducing 2-acetamido-4-((4-((3-fluorobenzyl)oxy)phenyl)amino)-4-oxobutanoic acid (10) to afford (S)-3-acetamido-N-(4-((3-fluorobenzyl)oxy)phenyl)-4-hydroxybutanamide (6); (d) chlorinating 6; and (e) cyclizing 6 to afford 1.

16. (S)-3-acetamido-N-(4-((3-fluorobenzyl)oxy)phenyl)-4-hydroxybutanamide (7).

* * * * *